US011331163B2

(12) United States Patent
Galili et al.

(10) Patent No.: US 11,331,163 B2
(45) Date of Patent: May 17, 2022

(54) UNIVERSAL HOLDER FOR AN INSERTABLE MEDICAL TOOL

(71) Applicant: XACT ROBOTICS LTD., Caesarea (IL)

(72) Inventors: Ben Galili, Atlit (IL); Frank Schenk, Tel Aviv (IL); Simon Sharon, Maayan Zvi (IL); Danna Perlman, Haifa (IL); Edna Gadon, Tel Aviv (IL)

(73) Assignee: XACT ROBOTICS LTD., Caesarea (IL)

( * ) Notice: Subject to any disclaimer, the term of this patent is extended or adjusted under 35 U.S.C. 154(b) by 561 days.

(21) Appl. No.: 16/330,317

(22) PCT Filed: Sep. 24, 2017

(86) PCT No.: PCT/IL2017/051066
§ 371 (c)(1),
(2) Date: Mar. 4, 2019

(87) PCT Pub. No.: WO2018/055621
PCT Pub. Date: Mar. 29, 2018

(65) Prior Publication Data
US 2019/0223977 A1 Jul. 25, 2019

Related U.S. Application Data

(60) Provisional application No. 62/495,759, filed on Sep. 23, 2016.

(51) Int. Cl.
*A61B 90/57* (2016.01)
*A61M 5/20* (2006.01)
(Continued)

(52) U.S. Cl.
CPC .......... *A61B 90/57* (2016.02); *A61B 17/3403* (2013.01); *A61H 39/08* (2013.01);
(Continued)

(58) Field of Classification Search
CPC ........ A61B 17/3403; A61B 2017/3405; A61B 90/11; A61B 90/57; A61B 34/30; A61H 2201/0192
See application file for complete search history.

(56) References Cited

U.S. PATENT DOCUMENTS 5,332,184 A * 7/1994 Davis .................. A61M 5/1415
24/525
7,008,373 B2 3/2006 Stoianovici et al.
(Continued)

FOREIGN PATENT DOCUMENTS

JP 2010531672 A 9/2010
WO 2009027848 A2 3/2009
(Continued)

OTHER PUBLICATIONS

International Search Report PCT/IL2017/051066 Completed Dec. 26, 2017; dated Dec. 28, 2017 3 pages.
(Continued)

*Primary Examiner* — Todd J Scherbel
(74) *Attorney, Agent, or Firm* — The Roy Gross Law Firm, LLC; Roy Gross

(57) ABSTRACT

A holder apparatus for enabling secure coupling of a variety of medical tool types, having different head member configurations, to a medical device. The apparatus has at least two housing portions that open and close to receive the head member, and an adjustment mechanism that adjusts to the height and/or shape of the head member, such that there is no relative movement between the housing portions and the head member. The adjustment mechanism may be a ratchet mechanism, a semi-flexible fastener, or a moldable material disposed on one or more of the housing portions. There may be a locking mechanism to lock together the housing portions, and a tightening mechanism to secure the grip of the housing portions on the head member. The housing portions
(Continued)

may be configured to allow removal of at least a portion of the medical tool from the device.

19 Claims, 16 Drawing Sheets

(51) Int. Cl.
*A61H 39/08* (2006.01)
*A61B 17/34* (2006.01)
*A61B 10/02* (2006.01)
*A61B 18/00* (2006.01)
*A61B 1/00* (2006.01)
*A61M 25/00* (2006.01)
*A61B 17/00* (2006.01)

(52) U.S. Cl.
CPC .................. *A61M 5/20* (2013.01); *A61B 1/00* (2013.01); *A61B 10/02* (2013.01); *A61B 18/00* (2013.01); *A61B 2010/0208* (2013.01); *A61B 2017/00486* (2013.01); *A61B 2017/3405* (2013.01); *A61H 2201/0192* (2013.01); *A61M 25/00* (2013.01)

(56) References Cited

U.S. PATENT DOCUMENTS

| | | | |
|---|---|---|---|
| 8,348,861 | B2 | 1/2013 | Glozman et al. |
| 8,663,130 | B2 | 3/2014 | Neubach et al. |
| 2008/0004481 | A1 | 1/2008 | Bax et al. |
| 2012/0190970 | A1 | 7/2012 | Velusamy et al. |
| 2012/0245456 | A1 | 9/2012 | Kim et al. |
| 2013/0182381 | A1 | 7/2013 | Gray et al. |
| 2016/0249991 | A1* | 9/2016 | Glozman ............ A61B 17/3403 606/130 |
| 2017/0258489 | A1 | 9/2017 | Galili et al. |

FOREIGN PATENT DOCUMENTS

| | | |
|---|---|---|
| WO | 2012063267 | 5/2012 |
| WO | 2016084092 | 6/2016 |
| WO | 2017203531 | 11/2017 |

OTHER PUBLICATIONS

Written Opinion of the International Searching Authority PCT/IL2017/051066 dated Dec. 28, 2017 5 pages.

* cited by examiner

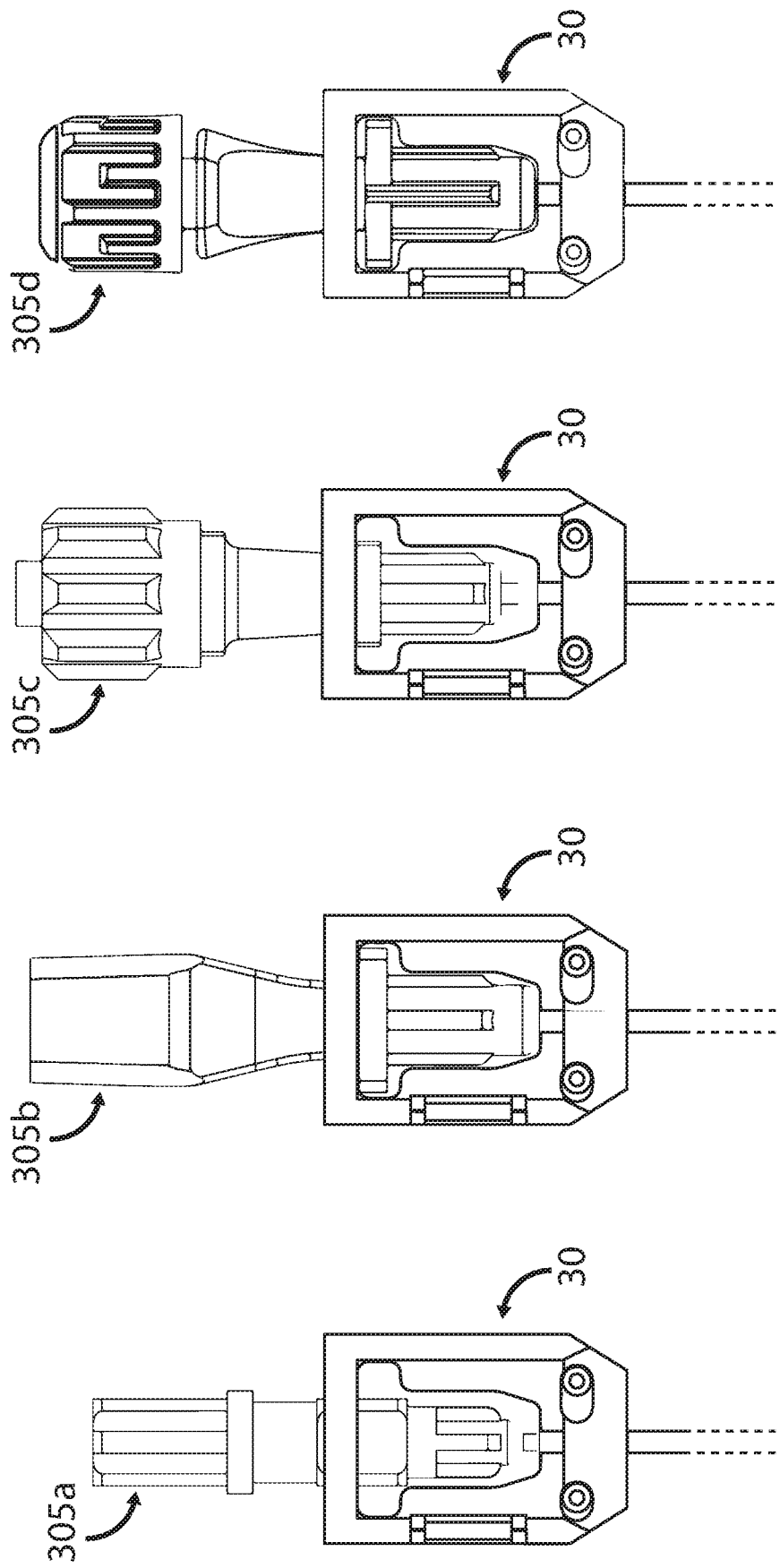

UNIVERSAL HOLDER FOR AN INSERTABLE MEDICAL TOOL

CROSS REFERENCE TO RELATED APPLICATIONS

This application is a National Phase of PCT Patent Application No. PCT/IL2017/051066 having International filing date of Sep. 24, 2017, which claims the benefit of priority of U.S. Provisional Application No. 62/495,759 filed on Sep. 23, 2016. The contents of the above applications are all incorporated by reference as if fully set forth herein in their entirety.

FIELD OF THE INVENTION

The present invention relates to medical tools used in diagnostic and/or therapeutic procedures, and more specifically to an apparatus for enabling secure coupling of a variety of medical tool types to a medical device.

BACKGROUND

Many routine treatments employed in modern clinical practice involve percutaneous insertion of medical tools, such as needles and catheters, for biopsy, drug delivery and other diagnostic and therapeutic procedures. The aim of an insertion procedure is to place the tip of an appropriate medical tool safely and accurately in a target region, which could be a lesion, tumor, organ or vessel. Examples of treatments requiring insertion of such medical tools include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

Guidance and steering of needles in soft tissue is a complicated task that requires good three-dimensional coordination, knowledge of the patient anatomy and a high level of experience. Therefore, image-guided automated (e.g., robotic) systems have been proposed for performing these functions. Among such systems are those described in U.S. Pat. No. 7,008,373 to Stoianovici, for "System and method for robot targeting under fluoroscopy", U.S. Pat. No. 8,348,861 to Glozman et al, for "Controlled Steering of a Flexible Needle", U.S. Pat. No. 8,663,130 to Neubach et al, for "Ultrasound Guided Robot for Flexible Needle Steering", U.S. patent application Ser. No. 15/027,439 to Glozman et al, for "Gripper for Robotic Image Guided Needle Insertion" and co-owned International Patent Application No. PCT/IL2017/050584 to Arnold et al, for "Automated Insertion Device".

Using an automated insertion device for manipulating a needle or other such medical instrument requires a holder apparatus which can grip the needle, typically the needle head, and couple it to the insertion device.

Co-owned U.S. patent application Ser. No. 15/531,435 to Galili et al, for "Insertion Guide", discloses a device for insertion of a flexible needle or other insertable medical instrument into a tissue. The device incorporates a collapsible support guide, which supports that part of the needle which has not yet penetrated the tissue, thus preventing it from buckling. The device further includes an arrangement which pulls the needle from its proximal end to provide sufficient force for the penetration process. The collapsible support guide may be a telescopic support tube, or a pair of flexible strips connected along at least a portion of their length and enclosing the needle along its uninserted length in order to support it, with a mechanism, such as counter-rotating rollers, at the distal end of the device to peel the strips from the needle as it is inserted. The device disclosed in U.S. Ser. No. 15/531,435 includes a holder apparatus, which secures together the needle head and the collapsible support guide, for example, the pair of flexible strips, such that counter-rotation of the strips at the distal end of the device will result in pulling of the needle from its proximal end toward the subject's body.

Thus, there is a need for a holder apparatus which can be used in conjunction with a variety of needle types having different needle gauges and needle heads of different shapes and sizes, to avoid limiting the users to a single needle type or requiring them to carry multiple holders, each compatible with a specific needle type.

In addition to being adaptable to different needle types, there is a need for a holder apparatus that allows access to the needle head during the medical procedure, for instance, in order to remove the needle's core and insert a biopsy needle therethrough.

Further, in some cases after the needle has been inserted into the subject's body, the physician may prefer to leave only the needle in place for the remainder of the medical procedure and remove all other components which are coupled to the needle and which may obstruct his/her view or actions. Thus, there is further a need for a holder apparatus which is disconnectable and removable from the needle head.

The disclosures of each of the publications mentioned in this section and in other sections of the specification, are hereby incorporated by reference, each in its entirety.

SUMMARY

The present disclosure describes a holder apparatus (also referred to hereinafter as "Needle Head Holder" or "NHH") used in medical procedures for coupling and securing a needle, or any other similar medical instrument, to an automated medical device, such as an insertion device.

The disclosed holder apparatus has a novel structure, which may be adjustable or moldable, such that it enables the holder apparatus to be universal. It can be appreciated that the term "universal", as used in the present disclosure, may not necessarily mean that the disclosed holder apparatus is compatible with all existing needle types, but that it is multi-compatible, i.e., it may be used with a variety of different needle types. Such variety of needle types may include needles of different gauges, having needle heads of different shapes and sizes. Thus, the user is not limited to a single needle type and/or required to carry multiple holders, each compatible with a specific needle type.

In some implementations, the holder apparatus may include at least one depression (or—socket), each being adapted to receive one or more needle head configurations. For example, each depression may correspond to the size and shape of a specific needle head configuration.

Once the needle is coupled to the holder apparatus, the holder apparatus is securely fastened to the needle head such that there is substantially no relative movement between the needle head and the holder apparatus.

In some implementations, the needle head holder may comprise a body portion for receiving the needle head, and a "door-like" side portion, which can be closed to secure the needle head therein. The side portion may be connected to the body portion of the NHH via a hinge such that it can be pivoted from an open position to a closed position, and vice versa. Alternatively, the side portion may be adapted to slide sideways using rail/s, for example. Once in the closed position, the coupling between the side portion and the body portion may be secured using a latch, a sliding pin, or any other suitable locking mechanism.

The needle head holder may further include a securing mechanism which can be adjusted, either manually or automatically, to the size and/or shape of the specific needle head in use, in order to efficiently secure the needle head to the needle head holder and allow use of a variety of needle types. In some implementations, the securing mechanism may include at least one semi-flexible gripper, such as a semi-annular gripper, which can be pushed open by the needle head as it is being inserted into the NHH by the user. In other implementations, the adjustable securing mechanism may include an inner layer of a moldable material, such as low-resilience polyurethane foam (or—"viscoelastic" polyurethane foam, memory foam), which can conform to the shape of the object pressed against it. Thus, insertion of the needle head into the NHH and/or locking of the NHH when in its closed state, presses the needle head against the moldable layer, resulting in the moldable layer assuming the shape of the needle head, such that there is substantially no relative movement between the needle head and the NHH.

In some implementations, the securing mechanism of the NHH may include a cover portion which can be moved in order to secure the needle head in the NHH. For example, the height of the cover portion relative to the base of the NHH may be adjustable, such that once the needle is in its proper position within the NHH, the cover portion is displaced toward the needle head until it contacts the proximal end of the needle head. The cover portion may be displaced toward the needle head using a sliding mechanism, for example, or a ratchet mechanism, which ensures that the cover portion cannot unintentionally move upwards and away from the needle head.

In some implementations, the securing mechanism may further include a tightening mechanism configured to tighten the grip of the NHH on the needle head. The tightening mechanism may be in the form of a rotatable knob and a rod passing through the NHH wall, such that rotation or pressing of the knob results in the rod pressing the needle head against the opposite inner wall of the NHH directly or against a moldable material disposed on at least the opposite inner wall.

Another exemplary tightening mechanism may include a zip-tie mechanism. The zip-tie mechanism may be combined with the cover portion of the NHH, such that once the needle head is properly positioned in the NHH, the cover portion is positioned over the needle head and a ridged strip of the cover portion is threaded through a dedicated locking member having an inner pawl. The strip is then pulled to tighten the grip of the cover portion on the needle head. In some implementations, the zip-tie mechanism may be provided unassembled, i.e., such that upon positioning of the needle head in the NHH, the user inserts the ridged strip into the locking member, thus closing the NHH, and he/she then pulls the strip to tighten the NHH's grip on the needle head.

In other implementations, the zip-tie mechanism may be provided pre-assembled, i.e., with the strip already inserted, to a certain extent, through the locking member. In such cases, the closing of the NHH may be achieved by means of a different mechanism, such as a snap-fit mechanism between two anchoring units at the distal end (or—base) of the NHH. Once the snap-fit connection is established, the user pulls the free end of the pre-inserted strip until the cover portion firmly secures the needle head in its position.

The needle head holder may be reusable such that a single holder may be used with different needles during a single procedure and/or during several medical procedures, or it may be disposable, such that it is discarded after a single use, so as to prevent possible cross-contamination between patients.

In some cases, for instance when a biopsy is performed, the procedure may require insertion of a hollow introducer with a solid core therein, the core is then removed and a biopsy needle is inserted. The disclosed needle head holder may be configured such that it allows access to the needle head during the procedure in order to remove the core and insert the biopsy needle into the patient's body through the introducer. In some implementations, the NHH may cover only the distal (lower) portion of the needle head, such that the proximal end of the needle head remains accessible during the medical procedure. In other implementations, as described hereinabove, the NHH may comprise a cover portion which is adjusted according to the height and/or shape of the needle head such that it maintains contact with the proximal end of the needle head and secures it in its place. The cover portion may be moved from its position, or even entirely removed from the needle head during the procedure, to allow the user access to the needle head. For example, the cover portion may be configured to be lifted from the needle head and then rotated sideways and away from the needle head, thus allowing access to the core and replacement of the core with a biopsy needle. In case a ratchet mechanism is employed, removal of the cover portion may require the user to disengage the locking pawl from the ratchet teeth, such as by pressing a release lever, prior to, and in some case also during, the removal of the cover portion from the needle head.

In some cases, once the needle is inserted into the target inside the patient's body, the physician/clinician may prefer to leave only the needle in place and disconnect it from the insertion device, since the insertion device may obstruct his/her view or actions. In some implementations, the NHH may be configured such that it can be disconnected from the insertion device while remaining coupled to the needle head. In other implementations, the NHH may be configured such that it can be de-coupled from the needle head while the needle remains in the patient's body. The NHH may be modular such that it can be disassembled in order to de-couple it from the needle head.

Implementations of the systems and devices described above may further include any of the features described in the present disclosure, including any of the features described hereinabove in relation to other system and device implementations.

One exemplary implementation of the present disclosure involves a device for securing a medical tool, selected from medical tools having different head member configurations (the term configuration as used throughout this disclosure including inter alia size and shape). Such a device may comprise two or more housing portions configured to receive a head member of any of these medical tools, and an adjustment mechanism configured to adjust at least one of the height and shape of at least a portion of the device according to at least one of the height and shape of the head member. At least one of the housing portions may be adapted for movement relative to at least another of the housing portions, to transition the device to at least one of from an open state to a closed state and from a closed state to an open state. When the two or more housing portions have received a head member and are in a closed state, and the adjustment mechanism has been activated, there is essentially no relative movement between the housing portions and the head member.

Such a device may further comprise a locking mechanism configured to lock together at least two of the housing portions when the device is in its closed state. Such a locking mechanism may comprise at least one of a latch, a locking pin and a snap-fit mechanism.

The adjustment mechanism of any of these implementations may comprise a ratchet mechanism. Such a ratchet mechanism may include ratchet teeth disposed on at least one of the housing portions, and a locking pawl in at least another of the housing portions, the locking pawl being configured to engage with the ratchet teeth. Such a device may further include a release member configured to disengage the locking pawl from the ratchet teeth. Any such ratchet mechanism may include an elongated element having ratchet teeth along at least a portion of its length and a receiving member having an opening for inserting a first end of the elongated element therethrough, and wherein the opening contains a pawl adapted to engage with the ratchet teeth of the elongated element upon insertion of the first end of the elongated element through the opening.

Alternatively, the adjustment mechanism may comprise a moldable material disposed on at least one of the two or more housing portions and configured to conform to the shape of at least a portion of the head member of the medical tool upon pressing of the head member against the moldable material. In another alternative implementation, the adjustment mechanism comprises a semi-flexible fastener coupled to an inner wall of at least one of the two or more housing portions.

In any of these implementations, at least two of the housing portions may be coupled together via a hinge, and at least one of the housing portions may include a cover element adapted to establish contact with the proximal end of the head member upon activation of the adjustment mechanism. The movement of any of the aforementioned housing portions may comprise at least one of linear movement and rotational movement. Any of these disclosed devices may further comprise one or more anchoring elements configured to attach a collapsible support guide of the medical tool to at least one of the housing portions. Such a collapsible support guide may comprise a pair of flexible strips connected along at least a portion of their length and having a central channel therebetween adapted to receive and support the medical tool. Any of these implementations may further comprise a tightening mechanism configured to secure the grip of the two or more housing portions on the head member of the medical tool, and the housing portions may advantageously be configured to allow removal of at least a portion of the medical tool from the device.

Yet another implementation of the present disclosure involves a device for securing a medical tool, selected from medical tools having different head member configurations. Such a device may comprise a first housing portion configured to receive at least a portion of a head member of any of the medical tools and a second housing portion coupleable to the first housing portion, the second housing portion being adapted to move relative to the first housing portion, either from an open state of the device to a closed state of the device or vice versa, or both. The device may further comprise an adjustment mechanism configured to adjust either the height or the shape of at least a portion of the device, or both, according to either the height or shape, or both, of the head member.

Such a device may further comprise a locking mechanism configured to lock together the first and second housing portions when the device is in its closed state. In either of these implementations, the adjustment mechanism and/or the locking mechanism may comprise a ratchet mechanism.

Such a ratchet mechanism may include ratchet teeth disposed on one of the first and second housing portions, and a locking pawl configured to engage with the ratchet teeth and being part of the other of the first and second housing portions. Such a device may further comprise a release member configured to disengage the locking pawl from the ratchet teeth. Furthermore, the proximal end of the one of the first and second housing portions may comprise a depression configured to receive the locking pawl when the device is in its open state.

Alternatively, the ratchet mechanism may include an elongated element having ratchet teeth along at least a portion of its length and a receiving member having an opening for inserting a first end of the elongated element therethrough, and wherein the opening includes therein a pawl adapted to engage with the ratchet teeth of the elongated element upon insertion of the first end of the elongated element through the opening.

In some implementations, the locking mechanism may comprise a latch disposed on one of the first and second housing portions, and a corresponding notch formed in the other of the first and second housing portions. Alternatively, such a locking mechanism may comprise a locking pin and a channel for receiving the locking pin, wherein the channel is formed in two or more interlocking parts of the first and second housing portions, each of the first and second housing portions including at least one of the two or more interlocking parts, such that upon moving the second housing portion to the closed state of the device, the locking pin is inserted into the channel to lock together the first and second housing portions. In further implementations, such a locking mechanism may comprise a snap-fit mechanism.

In any such implementations, the adjustment mechanism may include moldable material disposed on at least one of the first and second housing portions and configured to conform to the shape of at least a portion of the head member of the medical tool upon pressing of the head member against the moldable material. Such moldable material may be disposed on an inner wall of at least one of the first housing portion and the second housing portion. Alternatively, the adjustment mechanism may comprise a semi-flexible fastener coupled to an inner wall of at least one of the first housing portion and the second housing portion. Such a semi-flexible fastener may be annular and may be adapted to expand to the width of the head member upon receiving the head member therein.

In a novel arrangement, such implementations may further comprise a tightening mechanism configured to secure the grip of the first and second housing portions on the head member of the medical tool. Such a tightening mechanism may include a rotatable knob.

In any of these implementations, at least one of the first and second housing portions may include a cover element adapted to establish contact with the proximal end of the head member, and the first and second housing portions may be configured to allow removal of at least a portion of the medical tool from the device, when the device is in its open state.

In such a device, the first housing portion may include a base adapted to support the distal end of the head member of the medical tool. Such a base may be comprised of two units configured for coupling to each other, and the coupling between the two units may be established via a snap-fit mechanism.

In any of these implementations, the movement of the second housing portion relative to the first housing portion may comprise at least one of linear movement and rotational movement, and one of the first and second housing portions may include at least one guiding groove disposed along at least a portion of its length, and the other housing portion may include at least one protruding element adapted to move within the at least one guiding groove upon moving the second housing portion relative to the first housing portion. Further, in any of these implementations, the second housing portion may comprise a protrusion, and a wall of the first housing portion may comprise a niche adapted to receive the protrusion, and the rotational movement may comprise pivoting of the second housing portion relative to the first housing portion, upon the protrusion being received within the niche. The protrusion may be further adapted to move along the wall of the first housing portion upon linearly moving the second housing portion relative to the first housing portion.

Any such devices may further comprise one or more anchoring elements configured to attach a collapsible support guide of the medical tool to at least one of the first and second housing portions. Such a collapsible support guide may comprise a pair of flexible strips connected along at least a portion of their length and having a central channel therebetween adapted to receive and support the medical tool. Furthermore, at least one of the first and second housing portions may include a cover element configured to establish contact with the proximal end of the head member and to maintain the head member concentric with the central channel. Such a cover element may be pyramid-shaped. Any such anchoring elements may comprise one or more anchoring pins and one or more corresponding sockets, and the collapsible support guide may comprise one or more openings at its proximal end, through which the one or more anchoring pins are adapted to pass prior to being received by the one or more corresponding sockets.

Yet another novel implementation of this disclosure involves a device for securing a medical tool, selected from medical tools having different head member configurations. Such a device may comprise a first housing portion configured to receive a head member of any of the medical tools, the first housing portion including ratchet teeth disposed along at least a portion of the length of a wall of the first housing portion, and a second housing portion coupled to the first housing portion and including a pawl configured to engage with the ratchet teeth, a release member configured to disengage the pawl from the ratchet teeth, and a cover element adapted to contact the proximal end of the head member. In such a device, the second housing portion may be adapted to be moved relative to the first housing portion from an open state of the device to a closed state of the device and, upon activation of the release member, from a closed state of the device to an open state of the device.

In such implementations, the movement of the second housing portion relative to the first housing portion may comprise at least one of linear movement and rotational movement. Any of these implementations may further comprise one or more anchoring elements configured to attach a collapsible support guide of the medical tool to at least one of the first and second housing portions. Such a collapsible support guide may comprise a pair of flexible strips connected along at least a portion of their length and having a central channel therebetween adapted to receive and support the medical tool. Such a device may further comprise a cover element configured to maintain the head member concentric with the central channel.

A novel method of the present disclosure is used to secure a first medical tool, selected from medical tools having different head member configurations. Such a method may comprise:

(i) inserting the first medical tool, having a first head member, into an opening in at least one of one or more housing portions of a holder device, until the distal end of the first head member is supported by at least one of the housing portions;

(ii) displacing at least one of the housing portions to transition the holder device from an open state to a closed state, and (iii) adjusting at least one of the height and shape of at least a portion of the holder device according to at least one of the height and shape of the first head member, such that there is essentially no relative movement between the housing portions and the first head member.

Such a method may further comprise the steps of:
(i) displacing at least one of the housing portions to transition the holder device from a closed state to an open state;
(ii) removing the first medical tool from the holder device;
(iii) inserting a second medical tool, having a second head member having a configuration different from the configuration of the first head member of the first medical tool, into the opening, until the distal end of the second head member is supported by the at least one of the one or more housing portions;
(iv) displacing at least one of the housing portions to transition the holder device from an open state to a closed state; and
(v) adjusting at least one of the height and shape of at least a portion of the holder device according to at least one of the height and shape of the second head member, such that there is essentially no relative movement between the housing portions and the second head member.

In either of these methods, the adjusting may be executed using a ratchet mechanism. Such methods may further comprise the step of securing the grip of the one or more housing portions on the first and/or second head member of the first medical tool, using a tightening mechanism. Additionally, such methods may further comprise the step of locking the holder device upon transitioning the holder device from the open state to the closed state.

It is to be understood that the terms proximal and distal as used in this disclosure have their usual meaning in the clinical arts, namely that proximal refers to the end of a device or object closest to the person or machine inserting or using the device or object and remote from the patient, while distal refers to the end of a device or object closest to the patient and remote from the person or machine inserting or using the device or object.

It is also to be understood that although some examples used throughout this disclosure relate to a needle, needle head and needle head holder, this is done for simplicity reasons alone, and the scope of this disclosure is not meant to be limited to a needle, but is understood to include any medical tool/instrument which is insertable into the subject's body for diagnostic and/or therapeutic purposes, including an introducer, catheter, cannula, port, surgical tool, fluid delivery tool, or any other such insertable tool.

Further, for simplicity reasons alone, the term "needle" may refer throughout this disclosure either to the needle body intended to be inserted into the body or to the needle together with the needle head.

In addition, the terms "user", "doctor", "physician", "clinician", "technician", "medical personnel" and "medical staff" are used interchangeably throughout this disclosure and may refer to any person taking part in the performed medical procedure.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

FIGS. 3A-3D show an exemplary needle head holder coupled to four different needle types.

DETAILED DESCRIPTION

Figure 1:
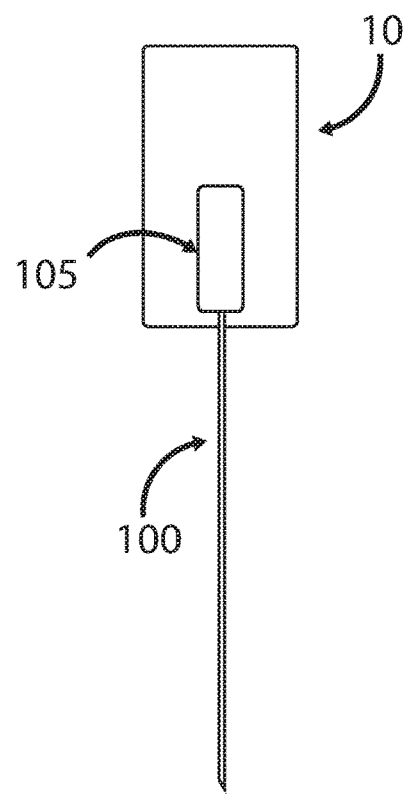
FIG. 1 shows a schematic diagram of a needle, needle head and needle head holder.

FIG. 1 shows a schematic diagram of a needle 100 with its needle head 105 and a needle head holder ("NHH") 10. The coupling between the NHH 10 and the needle head 105 may be through a top, bottom and/or side opening (not shown) in the NHH 10. The needle head holder 10 may be configured for gripping by a user, e.g., a physician, performing a manual medical procedure, such as a biopsy, or it may be configured for gripping by an automated device (not shown in FIG. 1) performing the medical procedure.

Figure 2:
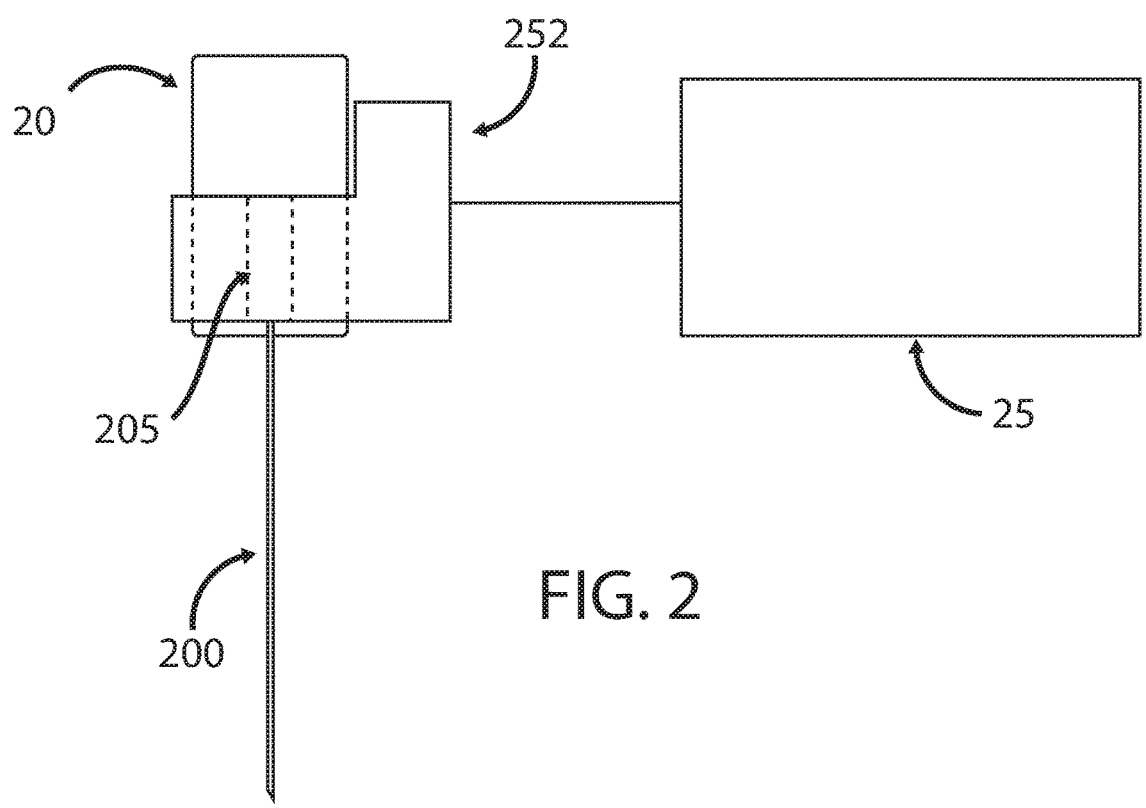
FIG. 2 shows a schematic diagram of a needle, needle head and needle head holder coupled to an end effector of an automated medical device.

FIG. 2 shows a schematic diagram of a needle 200 with its needle head 205, and a needle head holder 20 coupled to an end effector 252 of an automated medical device 25. The automated device 25 may be a robotic arm coupled to a dedicated cart or to the patient's bed, for example, or it may be a body-mounted robotic device, such as the device disclosed in the abovementioned International Patent Application No. PCT/IL2017/050584. The needle being coupled to the end effector 252 via the NHH 20 and not directly to the end effector 252 enables use of the same end effector, and thus the same medical device, with a variety of needle types.

In some implementations, the NHH 20 may a component of (or coupled to) an insertion module (not shown in FIG. 2), which in turn is coupled to the end effector 252. In such implementations, the insertion module may be coupled to the end effector by means of other component/s of the NHH 20, such that the NHH 20 is not directly coupled to the end effector 252. The insertion module and the end effector may each include at least part of the insertion mechanism, as disclosed, for example, in the abovementioned U.S. patent application Ser. No. 15/531,435.

In some implementations, the NHH 20 may be disposable and the end effector 252 reusable, such that the medical device with its end effector 252 can be used repeatedly with new needle head holders and with new needles.

FIGS. 3A-3D show an exemplary needle head holder 30 coupled to four different needle types, having four different needle heads 305a, 305b, 305c, 305d, which differ from each other in shape and size. It is to be understood that the NHH implementations described throughout this disclosure are not limited to those shown in FIGS. 3A-3D, and they may be used with any other needle type, including needles having electrical cables coupled to their needle heads, such as ablation needles, needles having optic fibers traversing therethrough, needles which induce ultrasonic vibrations, etc.

Reference is now made to FIGS. 4A-5D, which show exemplary implementations of a needle head holders which are configured such that they cover only a portion of the needle head, such that access to the needle head is maintained after it is coupled to the needle head holder. Such access may be required, for example, in biopsies, where the physician may first insert a hollow introducer with its solid core into the patient's body, and once the introducer reaches the target of the biopsy, the physician removes the core and inserts a biopsy needle to the target through the introducer.

Figure 4A:
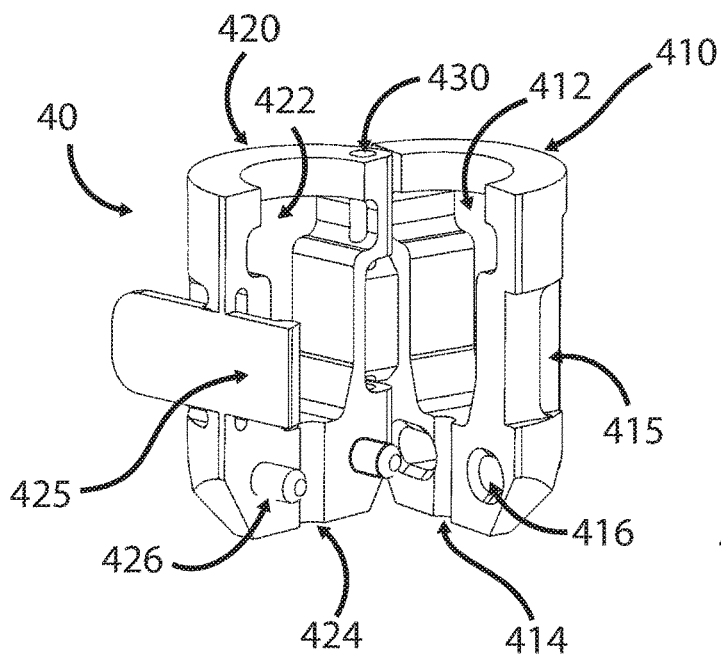
FIGS. 4A-4C show an exemplary needle head holder in its open state prior to coupling a needle thereto (FIG. 4A), in its open state after coupling a needle thereto (FIG. 4B), and in its closed state after securing the coupled needle thereto (FIG. 4C).

FIG. 4A shows a perspective view of an exemplary needle head holder 40 in its open state. The NHH 40 may be comprised of at least two portions, a receiving portion 410, to which the needle head (not shown in FIG. 4A) is inserted, and a securing portion 420, which is moved by the user once the needle head is in its proper position within the receiving portion 410, to close the NHH 40 and secure the needle head therein. It can be appreciated that, alternatively, portion 420 may be the receiving portion and portion 410 may be the securing portion. The needle head holder 40 may include a hinge 430, which allows the securing portion 420 to pivot from an open state to a closed state, and vice versa. The needle head holder 40 may further include a locking mechanism to secure the coupling between the securing portion 420 and the receiving portion 410 and maintain the NHH 40 in a closed state. The locking mechanism may include, for example, a latch 425 attached to the securing portion 420 and a notch 415 located in the receiving portion 410, such that upon closing the needle head holder 40, the latch 425 is caught by the notch 415, either automatically or manually by the user, and the needle head holder 40 remains closed until the latch 425 is released from the notch 415 by the user. It can be appreciated that the latch may otherwise be part of the receiving portion 410 and the notch part of the securing portion 420. In some implementations, the receiving and securing portions 410, 420 may include depressions 412, 422, respectively, which house the needle head. The depressions 412, 422 may correspond to the size and shape of a specific needle head or they may be configured to receive a variety of needle heads of different shapes and sizes, as will be described in detail with regard to FIGS. 5A-5D.

Figure 4B:
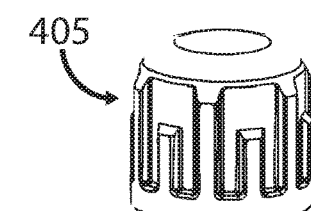
Figure 4C:
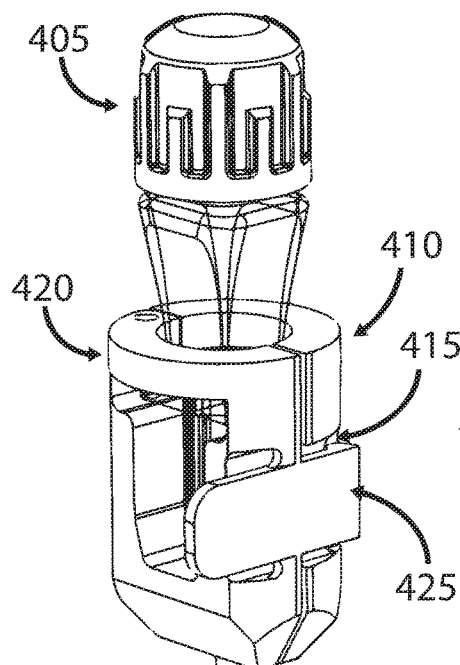

The NHH 40 may include a channel for receiving and enclosing at least the proximal portion of the needle therein. The channel may be located in either one of the receiving portion 410 or the securing portion 420, or it may be formed by the coupling of two corresponding grooves 414 and 424 in the receiving and securing portions 410 and 420, respectively, upon transitioning the NHH to the closed state, as shown in FIGS. 4A-4C. In some implementations, the channel may be sized to receive needles having a specific gauge. In other implementations, in which the NHH 40 is configured to receive a variety of needle heads of different shapes and sizes, the channel may be sized according to the largest needle gauge which can be used with the NHH 40.

As previously mentioned, the NHH 40 may be part of (or coupled to) an insertion module (not shown in FIG. 4A), which in turn is coupled to an end effector (not shown in FIG. 4A) of an automated insertion device. The insertion module may include at least part of the insertion mechanism. In some implementations, the insertion mechanism may include a flexible support guide, such as a pair of flexible strips (shown hereinbelow in FIG. 6) connected along at least a portion of their length and having a central channel therebetween, which receives the needle, the strips being adapted to peel away from the needle as it is being inserted into the patient's body, as disclosed, in the abovementioned U.S. patent application Ser. No. 15/531,435. In such implementations, the strips may be coupled at their proximal end to the NHH 40, together with the needle head, such that pulling strips towards the patient's body results in advancement of the needle towards the patient's body. The coupling of the strips to the NHH 40 may be via pins 426 located in the securing portion 410 and corresponding notches 416 in the receiving portion 420, as will be described in detail with regard to FIG. 7 below. It can be appreciated that the pins 426 may otherwise be located in the receiving portion 410 and the corresponding notches 416 in the securing portion 420.

FIG. 4B shows the needle head holder 40 of FIG. 4A after insertion of a needle 400, 405 into the receiving portion 410, prior to closing of the NHH 40. The needle head 405 is positioned within the dedicated depression 412 in the receiving portion 410, and the needle 400 is positioned in the groove 414 of the receiving portion 410, which together with the groove 424 of the securing portion 420, will form the channel housing the needle 400, upon closing the NHH 40.

FIG. 4C shows the needle head holder 40 in its closed state, with the needle head 405 and the proximal end of the needle 400 securely positioned therein. The latch 425 is coupled to the notch 415, to prevent the NHH 40 from unintentionally opening. The needle head holder 40 will remain closed until the user releases the latch 425 from the notch 415 and pivots the securing portion 420 away from the receiving portion 410.

Figure 5A:
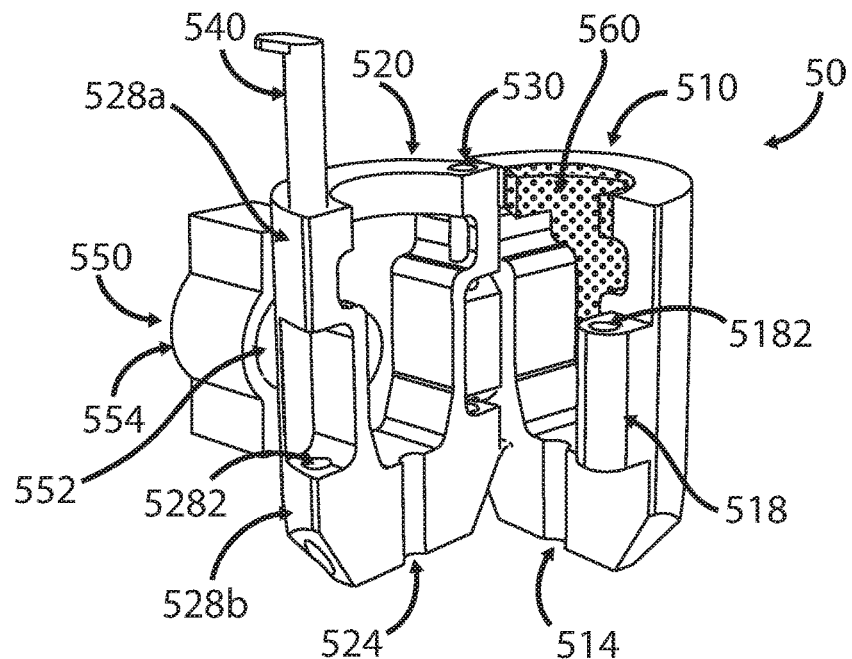
FIGS. 5A-5B show another exemplary needle head holder in its open state prior to coupling a needle thereto (FIG. 5A) and in its closed state after coupling and securing a needle thereto (FIG. 5B).
Figure 5B:
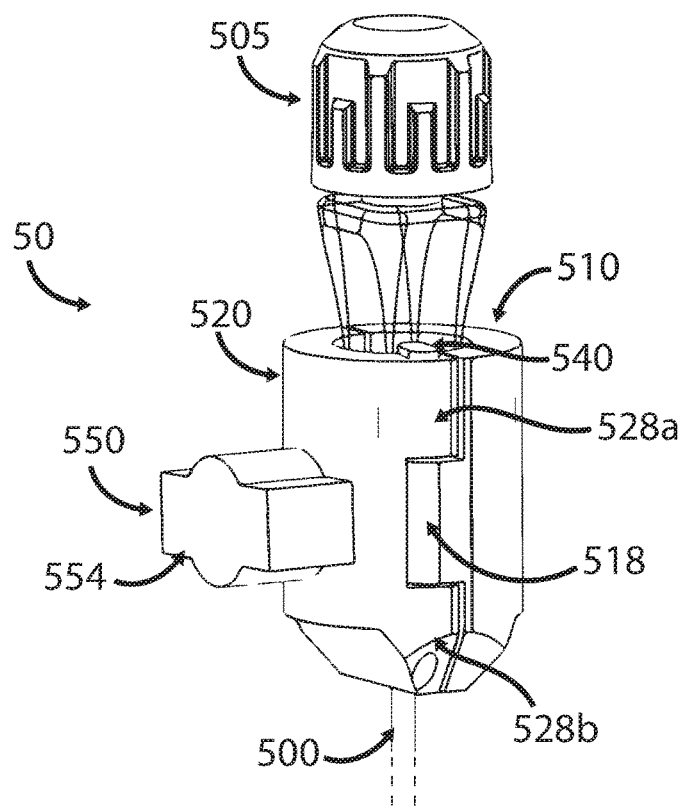

FIG. 5A shows another exemplary needle head holder 50, in its open state. The NHH 50 may be comprised of two portions, a receiving portion 510 and a securing portion 520. It may further include a hinge 530, which allows the securing portion 520 to pivot from an open state to a closed state and vice versa, and a pin locking mechanism to maintain the needle head holder 50 in a closed state. The receiving portion 510 and securing portion 520 may have interlocking parts 518 and 528a, 528b respectively, which have internal channels 5182, 5282 for receiving a locking pin 540 therein. When the NHH 50 is in the closed state, as shown in FIG. 5B, the internal channels 5182, 5282 align such that they form together a single channel which can receive substantially the entire length of the locking pin 540. Insertion of the locking pin 540 into the combined channel maintains the NHH 50 closed. It can be appreciated that although in FIG. 5A the receiving portion 510 has one interlocking part 518 and the securing portion 520 has two interlocking parts 528a and 528b, such that upon coupling the two portions 510, 520, the interlocking part 518 is positioned between interlocking parts 528a, 528b, this is merely an exemplary configuration, and other configurations, such as the receiving portion 510 having two interlocking parts and the securing portion 520 having one interlocking part to be positioned between the two interlocking parts of the receiving portion, or each portion having only one interlocking part, are within the scope of the present disclosure.

The needle head holder 50 may further include a tightening component 550, which secures the grip of the NHH 50 on the needle head (not shown in FIG. 5A). The tightening component 550 may be in the form of a rod 552 with a knob 554, the rod 552 passing through a wall of the NHH 50, for example the wall of the securing portion 520, such that pressing and/or rotating of the knob 554 results in the rod 552 pressing the needle head against the opposite inner wall of the NHH 50. The rod 552 and knob 554 may be a single component or they may be separate components coupled together. In some implementations, to prevent unintentional activation of the tightening component, whether for tightening or for loosening the NHH's grip on the needle head, the knob 554 must be first pressed against the rod 552 to couple them together and thus enable the tightening/loosening function, such as rotation of the rod 552 in case the rod is threaded. In some implementations, the NHH 50 may further include an inner layer of a moldable material 560, such as low-resilience polyurethane foam (or—"viscoelastic" polyurethane foam, memory foam), which can conform to the shape of the object being pressed against it. Thus, upon positioning the needle head in its place within the NHH 50, the needle head is pressed against the moldable layer, which assumes the shape of the needle head, such that there is no relative movement between the needle head and the NHH 50. The moldable layer 560 may be attached to the receiving portion 510, to the securing portion 520, or to both the receiving and the securing portions 510, 520.

FIG. 5B shows the needle head holder 50 of FIG. 5A in its closed state, with the needle head 505 and the proximal end of the needle 500 positioned therein. The interlocking parts 518, 528a, 528b are interlocked and the pin 540 has been pushed downward through the inner channels of the interlocking parts, such that the NHH 50 is securely locked and will remain locked until the user pulls the pin 540 upwards and out of at least interlocking parts 528b and 518.

Figure 5C:
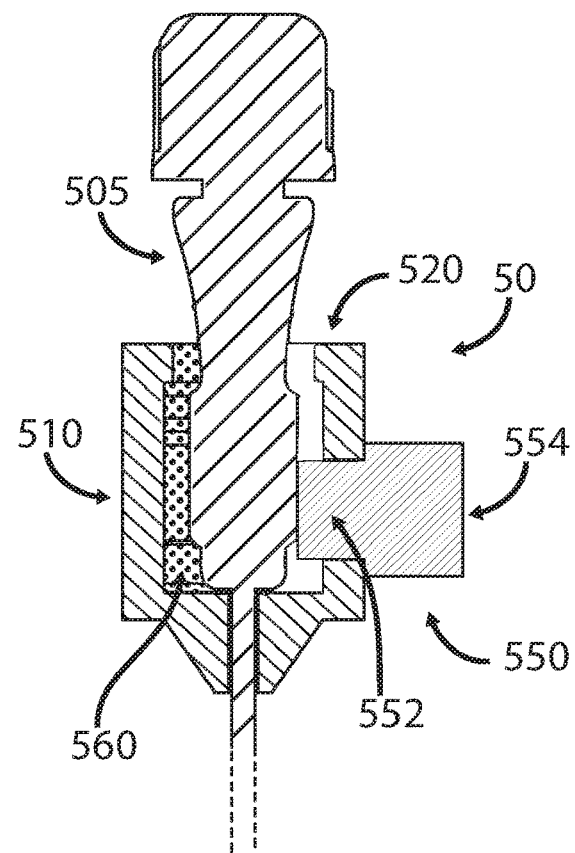
FIG. 5C shows a longitudinal cross-sectional view of the needle head holder and coupled needle of FIG. 5B.

FIG. 5C shows a longitudinal cross-sectional view of the NHH 50 in a closed state, after the knob 554 has been rotated/pressed such that the rod 552 holds at least a portion of the needle head 505 against the moldable layer 560 of the receiving portion 510. As a result, the moldable layer 560 assumes the shape of the needle head 505, or a portion thereof, and prevents undesired movement of the needle head 505. In some implementations, closing of the NHH 50 is sufficient for pressing the needle head 505 against the moldable layer 560 such that there is substantially no relative movement between the needle head 505 and the NHH 50. In such implementations, there is no need for an additional tightening component.

Figure 5D:
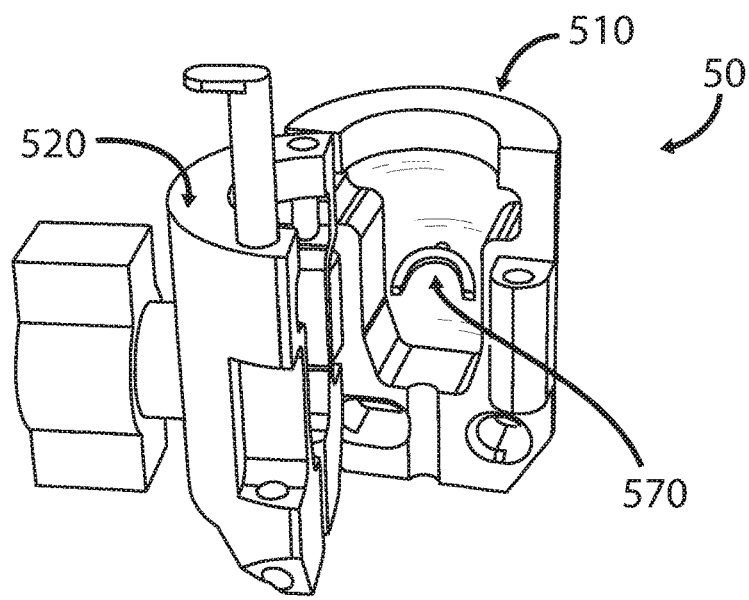
FIG. 5D shows a perspective view of a needle head holder having a semi-flexible fastener therein.

FIG. 5D shows a perspective view of the NHH 50, which instead of memory foam includes a fastener 570 to grip the needle head. The fastener 570 may be semi-flexible and it may have a semi-annular shape, such that it can be pushed open by at least a portion of the needle head as it is being inserted into the NHH 50 and grip the needle head, or a portion thereof. The fastener 570 may otherwise be in the form of one or more spring elements (not shown), which may be attached to the inner wall of either the receiving portion 510 or the securing portion 520. If the spring elements are attached to the receiving portion 510, then they are compressed by the needle head as its it being inserted into the NHH 50. If the spring elements are attached to the securing portion 520, then they are compressed against the needle head as the securing portion is being moved by the user to the closed position. The spring elements are then maintained in a compressed state, pushing the needle head against the securing (or the receiving) portion as long as the two portions of the NHH 50 are coupled together. Thus, different needle heads can be captured and held in place by the same needle head holder. It can be appreciated that spring element/s may also be used in conjunction with moldable material, such that they are coupled to the inner wall of the securing portion, for example, while the moldable material is provided on the inner wall of the receiving portion, and when the NHH is in its closed state, the spring element/s maintain the needle head pressed against the moldable material.

Reference is now made to FIGS. 6-13C, which show exemplary implementations of needle head holders which secure the needle head by supporting its bottom (distal) end and closing on its proximal end, such that they can be moved away from the proximal end of the needle head to allow access to the needle head after it is coupled to the needle head holder.

As previously mentioned, the needle head holder may be part of (or coupled to) an insertion module, which in turn is coupled to an end effector of a device for inserting a medical tool into a subject's body.

Figure 6:
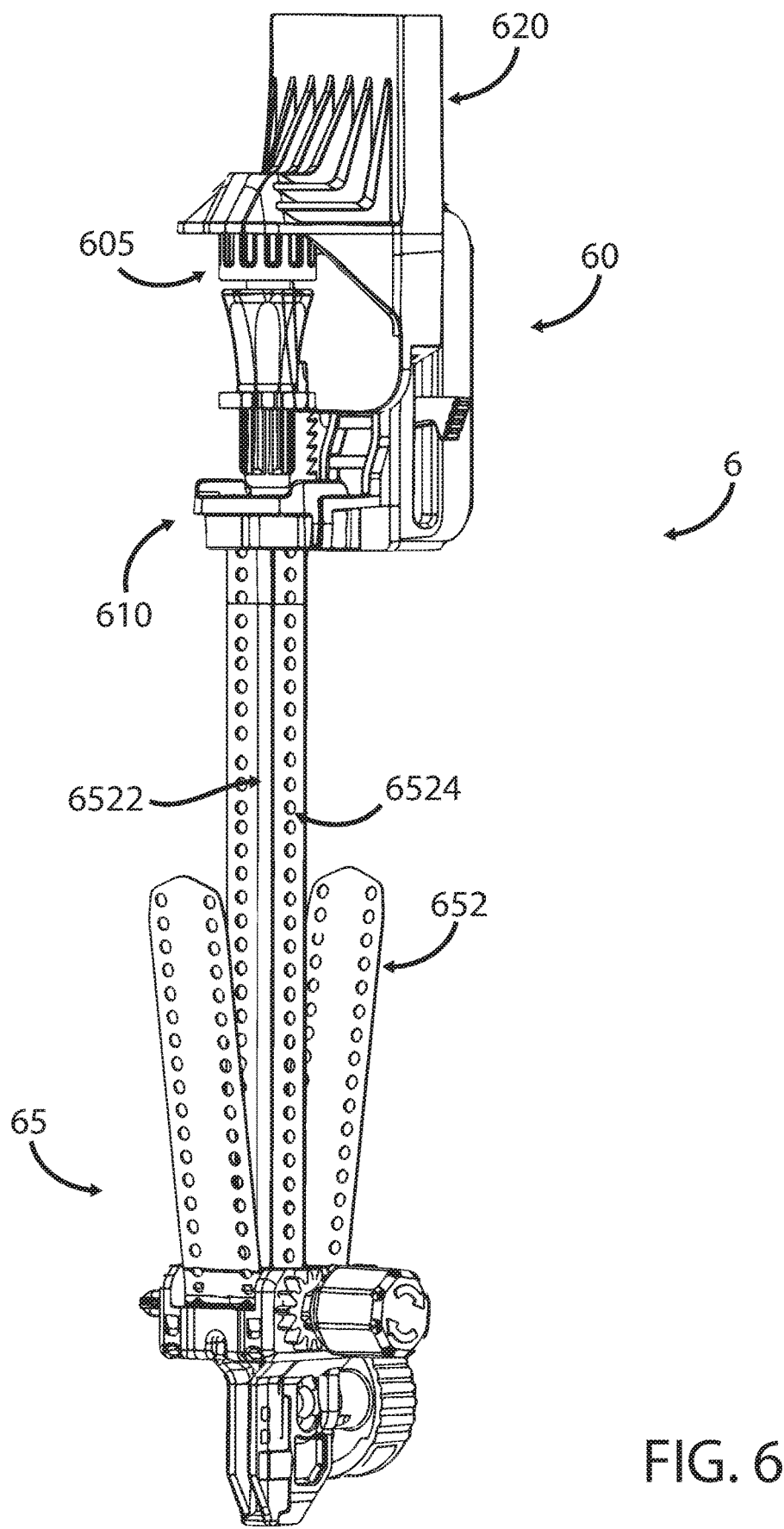
FIG. 6 shows a perspective view of an exemplary needle head holder having an adjustable cover portion, and an insertion module.

FIG. 6 Shows a perspective view of a needle head holder 60 which is part of an insertion module 6. The NHH 60 may be an integral part of the insertion module 6, or it may be a separate unit coupled to the insertion module 6. As also previously mentioned, the insertion module 6 may include at least part of the insertion mechanism 65. In some implementations, the insertion mechanism 65 may include a pair of flexible strips 652 connected along at least a portion of their length and having a central channel 6522 therebetween, to receive and enclose the needle therein. The insertion mechanism 65 may further include a pair of rollers (not shown) disposed on either side of the pair of flexible strips, and interacting therewith, such that counter-rotation of the pair of rollers causes the pair of flexible strips 652 to move between the pair of rollers. The engagement of the rollers with the strips 652 may be by means of perforations 6524 running along at least a portion of the length of the strips 652 and corresponding protrusions on the rollers. Coupling of both the strips 652 and the needle head 605 to the NHH 60 causes the needle to advance toward and into the body of the patient together with the strips 652 as they are being pulled toward the patient's body. The strips are adapted to peel away from the needle as it is being inserted into the patient's body, all as disclosed in the abovementioned U.S. patent application Ser. No. 15/531,435.

The needle head holder 60 may comprise a receiving portion 610, which supports the distal end of the needle head 605 and anchors the proximal ends of the strips 652 thereto, and a securing portion 620, which is displaced by the user once the needle head 605 is in its proper position, until it establishes contact with the proximal end of the needle head 605 and secures it within the NHH 60. The receiving portion 610 and the securing portion 620 may be two separate pieces provided pre-assembled or configured for assembly by the user.

Figure 7:
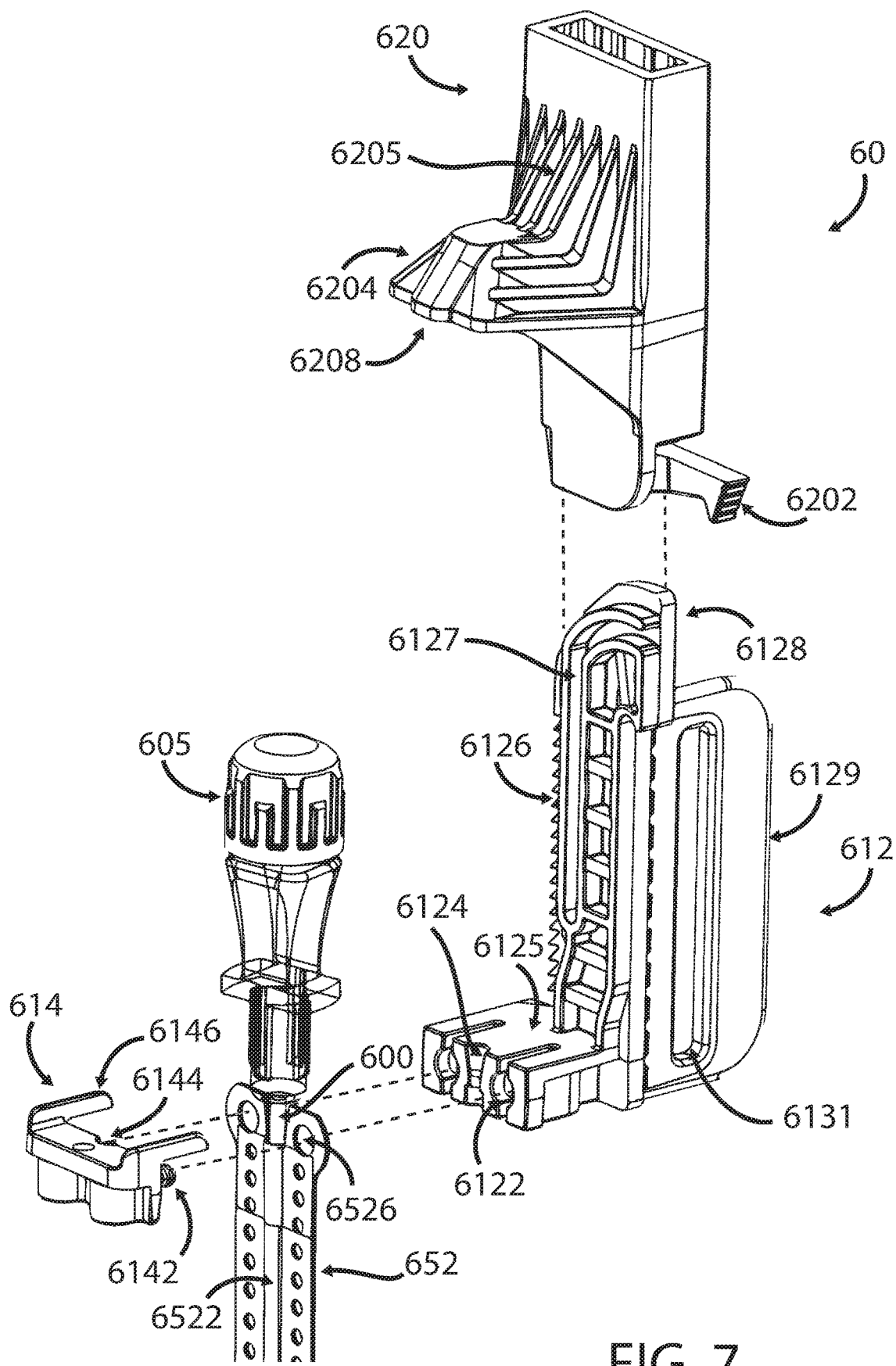
FIG. 7 shows an exploded view of the needle head holder of FIG. 6.

FIG. 7 shows an exploded view of the needle head holder 60 with the needle 600 and needle head 605, and with the strips 652 of the insertion mechanism. The receiving portion of the NHH 60 may include a body portion 612 and an anchoring portion 614, which are coupled together to anchor the proximal end of the strips 652 to the NHH 60. The coupling of the body and anchoring portions 612, 614 may be established, for example, using a snap-fit mechanism. The anchoring portion 614 may include one or more anchoring pins 6142, which are passed through one or more holes 6526 in the proximal end of at least one of the strips 652 and then mate with corresponding sockets 6122 in the base 6125 of the body portion 612, with the strips 652 being anchored therebetween. It can be appreciated that the anchoring pins 6142 may alternatively be part of the body portion 612 and the sockets 6122 part of the anchoring portion 614. It can further be appreciated that the strips 652 may be coupled to the NHH 60 using any other suitable means.

The body and anchoring portions 612, 614 may include a channel for enclosing the proximal end of the needle 600 therein. The channel may be located in one of the body or anchoring portions 612, 614, or it may be formed by corresponding grooves 6124, 6144 in the body and anchoring portions 612, 614, respectively, upon coupling of the two portions. In some implementations, the channel may be sized (e.g., its radius) to receive needles having a specific gauge. In other implementations, the NHH 60 is configured to receive a variety of needle types and the channel may be sized according to the largest needle gauge which can be used with the NHH 60. In some implementations, the proximal portion of the channel may have a conical shape in order to ease the insertion of the needle 600 into the central channel 6522 of the strips 652 through the receiving portion's channel. The proximal portion of the strips' central channel 6522 may also have a conical shape.

The anchoring portion 614 may further include one or more guides 6146 which the user places on the base 6125 of the body portion 612 and then slides them along the base 6125 until the anchoring pins 6142 are properly snapped into the sockets 6122. The guides 6146 assist in aligning the body and anchoring portions 612, 614, and establishing the snap fit connection between the two portions.

The coupling between the securing portion 620 and the body portion 612 of the receiving portion may be such that the two portions can be coupled and decoupled by the user, or it may be such that the two portions remain coupled at all times and cannot be disconnected from each other, however they can be moved and/or rotated relative to each other, while remaining coupled. The relative movement between the securing portion 620 and the body portion 612 may be enabled via a linear ratchet mechanism, such that movement of the securing portion 620 down the receiving portion 610, i.e., toward the needle head 605, is substantially unrestricted, and movement of the securing portion 620 in the opposite direction, i.e., upward and away from the needle head 605, is restricted and requires a releasing action to be enabled. Since, in some implementations, securing both the strips 652 and the needle head 605 to the NHH 60 is essential for successful insertion of the needle into the subject's body, as it operatively couples the needle to the strips 652, then if the grip of the needle head 605 is released, activation of the insertion mechanism may de facto disable the NHH 60. In such a case, activation of the insertion mechanism may result in displacement of only the strips 652 and the NHH 60 toward the subject's body, while the needle remains in its place.

In some implementations, the body portion 612 may include ratchet teeth 6126 having a slope in the forward (downward) direction, and the securing portion 620 may include a locking pawl (not shown in FIG. 7), which engages with the ratchet teeth 6126 and thus prevents unintentional movement of the securing portion 620 upward and away from the needle head 605. Release of the locking pawl from the ratchet teeth 6126, to enable upward movement of the securing portion 620, may be achieved by means of a release lever 6202. The release lever 6202 may be integral with the locking pawl or it may be a separate component coupled to the locking pawl.

The movement of the securing portion 620 along the body portion 612 may be solely linear or the body portion 612 may include an angular section, tilted or curved, at its proximal end 6128, such that when in the open state, the securing portion 620 is tilted and does not prevent or get in the way of inserting the needle into the NHH 60 and/or removing the needle's core from the NHH 60, for example. The body portion 612 may include one or more grooves 6127 to guide the movement of the securing portion 620 along the curved path, as will be described in detail hereinbelow with regard to FIG. 9A.

Moving the securing portion 620 along the body portion 612 enables adjustment of the height of the NHH 60, such that the NHH 60 can be used with a variety of needle types and other insertable medical tools, having needle heads of various lengths.

The body portion 612 may include a handle 6129 having a slit 6131 through which the release lever 6202 is passed. Gripping the handle 6129 may facilitate the user when pressing the release lever 6202 so as to release the locking pawl from the ratchet teeth 6126 and move the securing portion 620 upward and away from the needle head 605.

The securing portion 620 may include a cover element 6204 which maintains contact with the proximal end of the needle head 605 upon moving the securing portion 620 toward the needle head 605, such that the needle head 605 is effectively clamped between the base 6125 of the body portion 612 and the cover element 6204 of the securing portion 620. In some implementations, the cover 6204 may be shaped such that the needle head 605 is maintained concentric with the strips' central channel 6522 independently of the needle head's shape and size. For example, the cover 604 may be shaped as a pyramid having a longitudinal axis which is aligned with the longitudinal axis of the channel 6522, and a rectangle transverse cross-section, which is largest at its base and smallest at its top portion, such that the contact between the cover 6204 and the needle head 605 is realized via a plurality (in this case, four) of tangent points (or lines), and the inner shape of the cover 6204 need not necessarily correspond to the shape of one specific needle head shape. Such a pyramid shape, together with the capability to adjust the height of the securing portion 620 relative to the body portion 612, as will be described in detail hereinbelow, enables using the NHH 60 with a variety of different medical instruments. It can be appreciated, however, that the cover 6204 is not limited to a pyramid shape, and it may have any other shape having similar advantages, e.g., a dome shape, a cone shape.

In some implementations, the cover 6204 may further include one or more grooves 6208 for receiving corresponding protrusion/s in certain needle head types, such as for providing indication as to the orientation of the needle. For example, the location of a protrusion on the head of a beveled needle may correspond to the location of the tip of the bevel. Thus, in case the orientation of the needle is of significance to the procedure, or may influence it in any way, the position of the groove 6208 on the cover 6204 is such that needle head can only be placed in the NHH 60 in the desired orientation. The cover element 6204 may further include ridges/ribs 6205 for structural reinforcement.

Figure 8A:
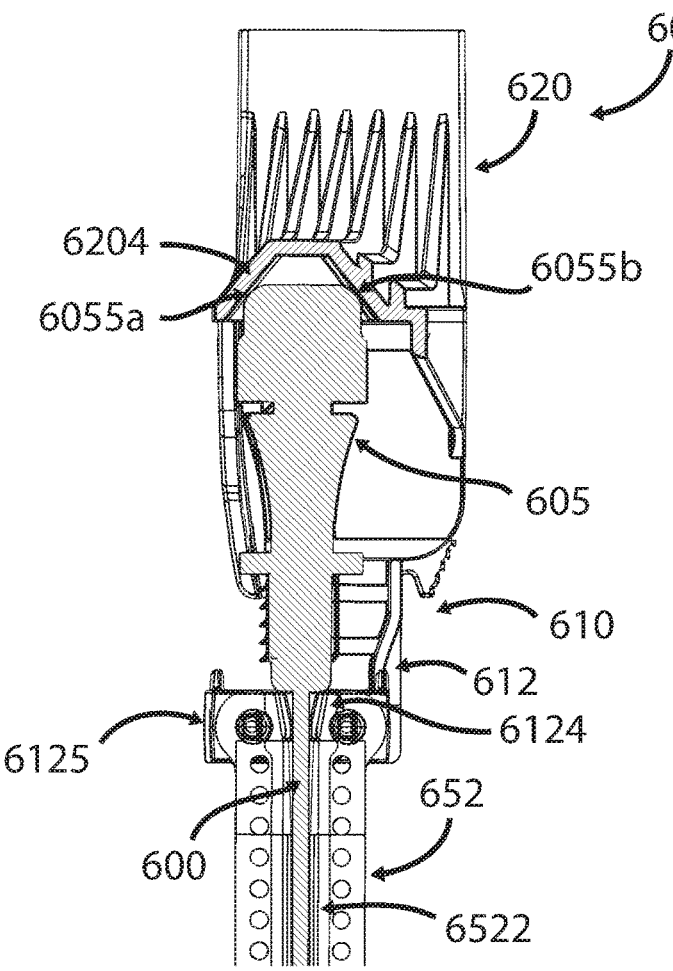
FIG. 8A shows a longitudinal cross-sectional view of the needle head holder of FIG. 6.

FIG. 8A shows a longitudinal cross-sectional view of the needle head holder 60 with the strips 652 attached and the needle 600, 605 inserted thereto. As previously mentioned, the receiving portion 610 of the needle head holder 60 may have a channel for inserting the needle 600 into the central channel 6522 of the strips 652 therethrough. The channel may be formed via the coupling of corresponding grooves in the body and anchoring portions (only groove 6124 of the body portion 612 is shown in FIG. 8A). Further, the proximal portion of the grooves 6124, and thus the proximal portion of the channel, may have a conical shape, to ease the insertion of the needle 600 into the central channel 6522 of the strips 652 through the receiving portion's channel.

Also shown in FIG. 8A is the cover element 6204 and its interface with the proximal end of the needle head 605. The user moves the securing portion 620 relative to the body portion 612, until the cover 6204 contacts the needle head 605, such that the needle head 605 is then clamped between the base 6125 of the body portion 612 and the cover element 6204 of the securing portion 620. In some implementations, the cover 6204 may be shaped, for example, as an adjustable dome (not shown). In the implementation shown in FIG. 8A the cover 6204 is shaped as a pyramid, which enables using the NHH 60 with various needle types having needle heads of various shapes and sizes, since the contact between the cover 6204 and the proximal end of the needle head 605 is established via a plurality of tangent points (or lines) 6055a, 6055b, the location of which may vary according to the shape and size of the needle head in use.

Figure 8B:
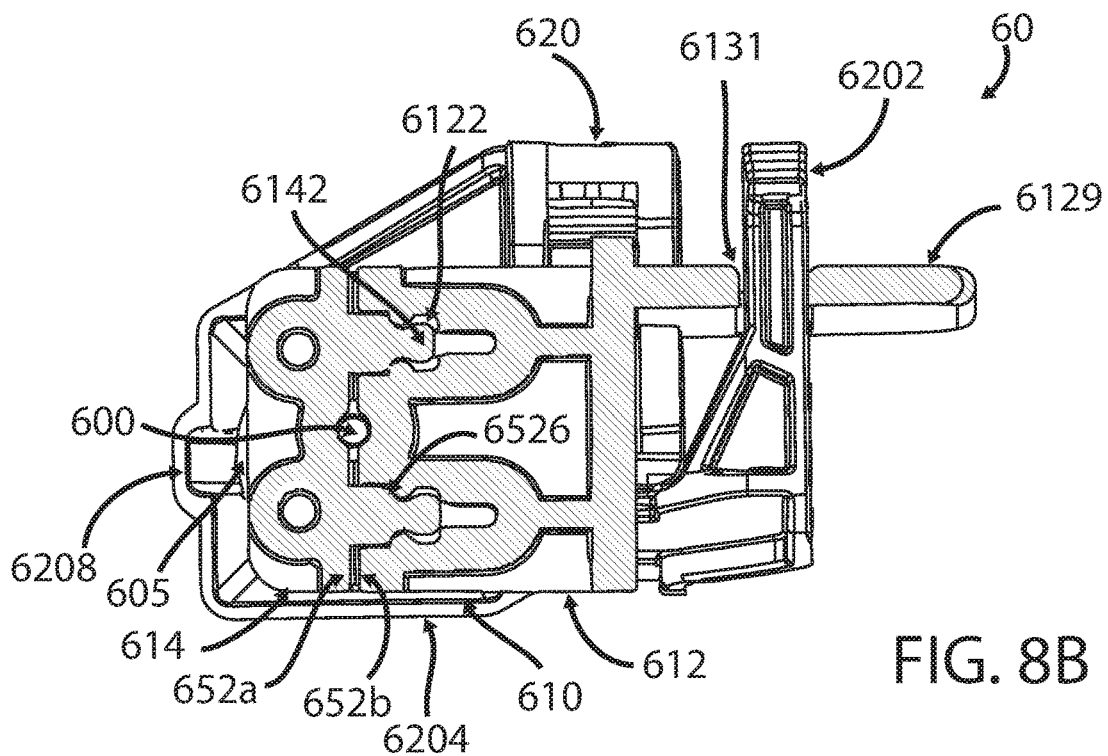
FIG. 8B shows a transverse cross-sectional view of the needle head holder of FIG. 6.

FIG. 8B shows a transverse cross-sectional view of the needle head holder 60 with the strips 652a, 652b attached and the needle 600, 605 inserted thereto. As previously mentioned, the coupling of the body and anchoring portions

612, 614 of the receiving portion 610 may be established via a snap-fit mechanism. The anchoring portion 614 may include anchoring pin/s 6142 that are passed through hole/s 6526 in at least one of the strips 652a, 652b, and then mate with corresponding socket's 6122 in the body portion 612, with the strips 652a, 652b being anchored therebetween.

In some cases, once the needle is inserted into the target inside the patient's body, the physician/clinician may prefer to leave only the needle in place and disconnect it from the insertion device, since the insertion device may obstruct his/her view or actions. In case the insertion device is body-mounted, the physician/clinician may wish to remove it from the patient's body altogether, while leaving the needle itself inside the patient's body. In such cases, the NHH may be configured such that the user can disconnect it from the insertion device, and the user can then remove the insertion device from the patient's body, while the NHH remains coupled to the needle head. Alternatively, the NHH may be configured such that it can be decoupled from the needle, so that the needle has no components attached to it for the remainder of the medical procedure. The NHH may be decoupled from the needle after it has been disconnected from the insertion device, or, in some implementations, the NHH may be separable into at least two parts, such that decoupling the NHH from the needle and removal of the insertion device can be executed in a single action, as described hereinafter.

Decoupling the NHH 60 from the needle may be achieved by disconnecting the body and anchoring portions 612, 614 from one another. In some implementations, the body portion 612 and/or the anchoring portion 614 may include a release member (not shown) to assist in the decoupling of the two portions. In other implementations, the body portion 612 and/or the anchoring portion 614 may be manufactured from a semi-flexible material, such that mutual pressing on the sides of the two portions enables pulling them apart. In further implementations, in which the NHH 60 is part of an insertion module, as shown in FIG. 6 hereinabove, the insertion module may be modular, such that the entire insertion module can be separated along its longitudinal axis, as described in the abovementioned U.S. patent application Ser. No. 15/531,435. In such implementations, the disconnecting of the different parts of the insertion module may commence at the insertion mechanism housing, which also holds the two strips after they peel away from the needle and from each other. The housing may have a release member, which the user activates in order to separate the housing, and the insertion mechanism therein, into two separate parts. The user then pulls the two parts away from each other, thus detaching the two strips from each other in the section between the insertion mechanism and the NHH 60, in which they are still attached to each other and enclose the needle in their central channel. The user then continues to pull the two parts away from each other, until the body portion 612 and the anchoring portion 614 disconnect from one another, thus completing the disconnection of the two parts of the insertion module from each other and from the needle 600, which remains in its position within the patient's body. Since the needle 600 is enclosed within the channel formed between the strips 652a, 652b, but it is not connected to the strips, or to any other component of the insertion module, disconnection of the two parts of the insertion module from one another does not apply on the needle 600 any major forces which may cause it to move from its position. In some implementations, one part of the insertion module remains coupled to the insertion device's end effector, such that disconnection of the two parts of the insertion module from one another de facto disconnects the insertion device from the needle, with no need for another disconnection action. In case of a body mounted insertion device, disconnection of the two parts of the insertion module from one another allows removal of the insertion device from the subject's body, with no need for another disconnection action.

Also shown in FIG. 8B is the release lever 6202, the pressing of which lifts the locking pawl of the securing portion 620 from the ratchet teeth of the body portion 612, thereby allowing the user to move the securing portion 620 away from the needle head 605. The release lever 6202 may be positioned within a slit 6131 in the handle 6129 of the body portion 612, so as to restrict the movement of the release lever 6202.

FIG. 8B further shows a partial bottom view of the pyramid-shaped cover element 6204 of the securing portion 620. The cover 6204 may include one or more grooves/channels 6208 which can receive corresponding protrusions in certain needle head types.

Figure 9A:
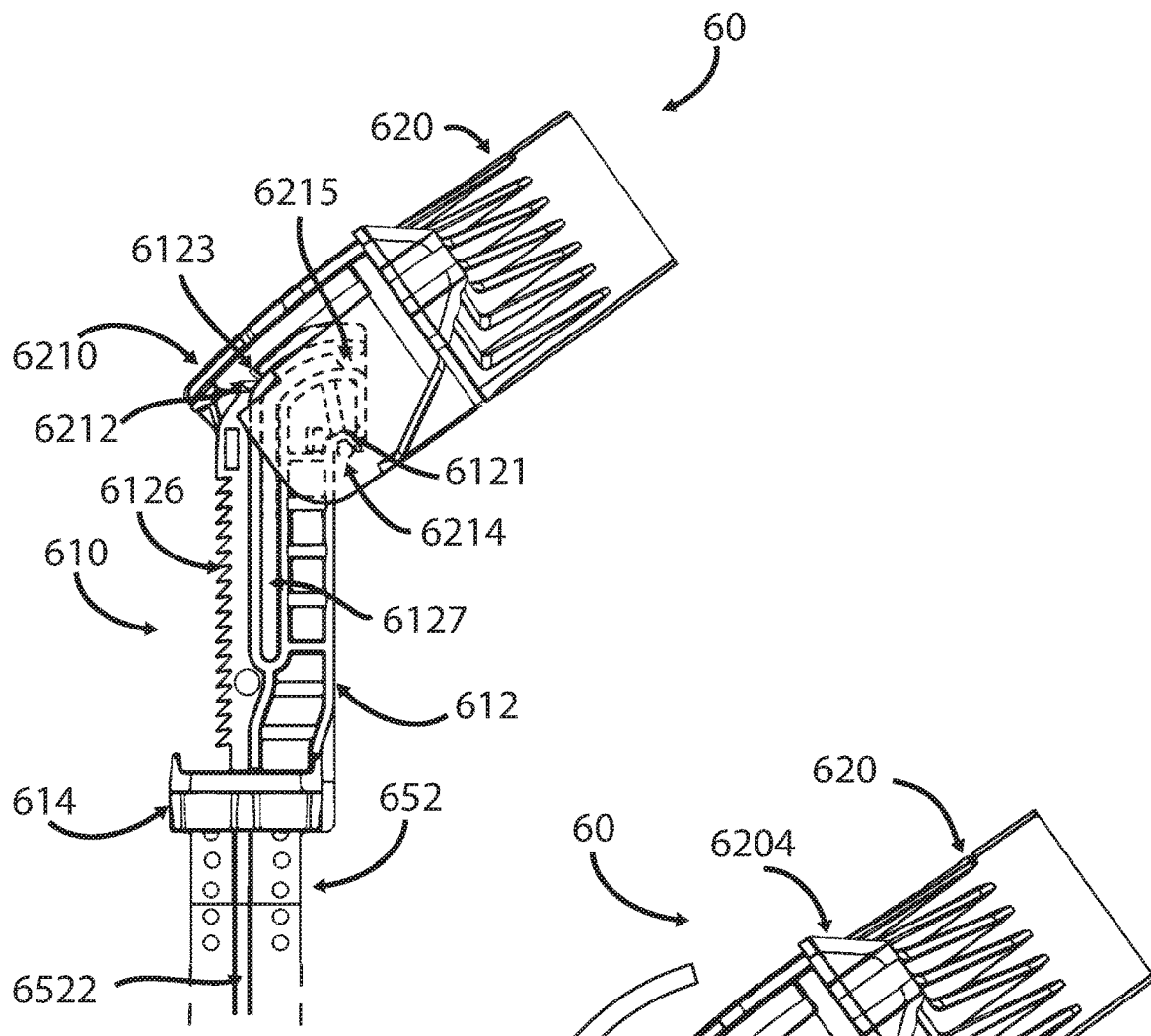
FIG. 9A shows the needle head holder of FIG. 6 in an open state, prior to coupling the needle to the needle head holder.

FIG. 9A shows the needle head holder 60 in its open state, prior to insertion of the needle into the central channel 6522 of the strips 652 and securing of the needle head to the NHH 60. The relative movement between the securing portion 620 and the receiving portion 610 may be via a ratchet mechanism. The body portion 612 of the receiving portion 610 may include ratchet teeth 6126 and the securing portion 620 may include a locking pawl 6210 having teeth 6212 which can engage with the ratchet teeth 6126. The securing portion 620 may further include a release lever (not shown in FIG. 9A), the pressing of which disengages the locking pawl 6210 from the ratchet teeth 6126, and thus enables controlled upward movement of the securing portion 620 along the body portion 612. The movement of the securing portion 620 along the body portion 612 (upward/downward) may be solely linear or it may include a curved section, at the proximal end of the body portion 612, to ensure that when the NHH 60 is in the open state, the securing portion 620 does not interfere with the insertion of the needle into the NHH 60 or prevent access to the needle head when such access is needed.

The securing portion 620 may include a pin (or—protrusion) 6214, which allows the pivoting of the securing portion 620 at the proximal end of the body portion 612. In some implementations, the pin 6214 moves along the outer wall of the body portion 612 as the securing portion 620 is being moved linearly along the body portion. When the user wishes to open the NHH 60, he/she moves the securing portion upwards along the body portion 612, until the pin 6214 is received within a dedicated niche 6121 in the outer wall of the body portion 612, which may be formed by curving of the outer wall. The pin 6214 then serves as the rotation axis for the securing portion 620.

The body portion 612 may further include one or more grooves 6127 and the securing portion 620 may include one or more protrusions/pins 6215 fitted within the groove/s 6127, to guide the movement of the securing portion 620 along the curved path.

The coupling between the receiving and the securing portions 610, 620 may be such that the two portions can be disconnected and reconnected by the user, or it may be such that the two portions can be displaced relative to each other but remain connected at all times. In the latter case, in order to prevent the securing portion 620 from disconnecting from the receiving portion 610 when the NHH 60 is in an open state, the body portion 612 of the receiving portion 610 may include a depression/gap 6123 which de facto serves as another ratchet tooth, similar to the ratchet teeth 6126, to capture the teeth 6212 of the locking pawl 6210 of the securing portion 620, in order to prevent its further movement away from the body portion 612.

Figure 9B:
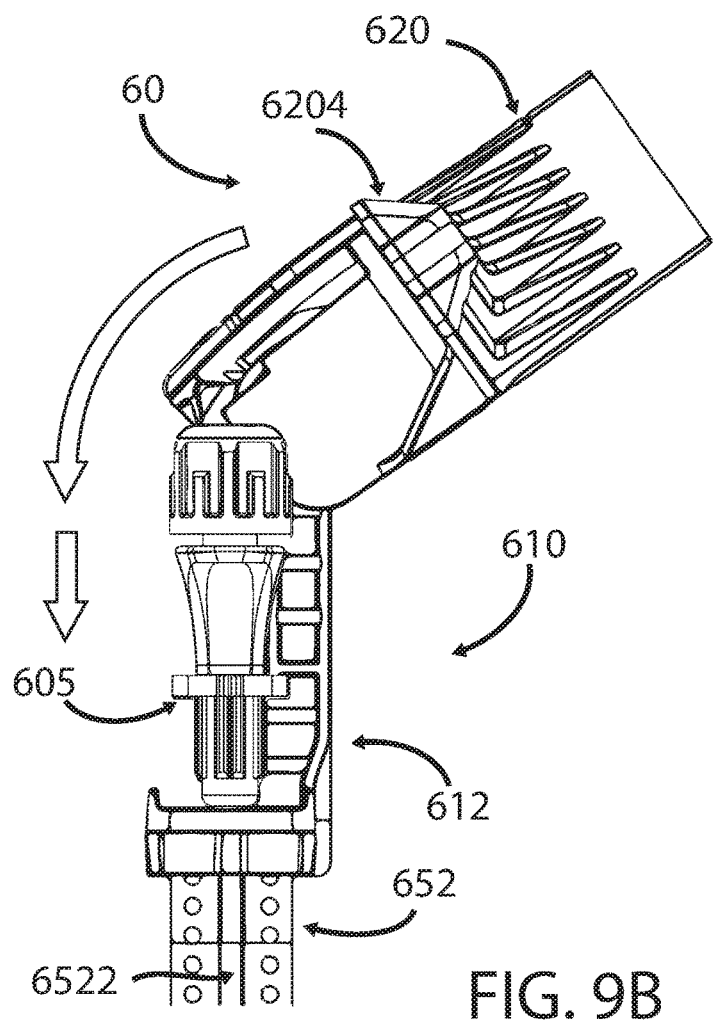
FIG. 9B shows the needle head holder of FIG. 6 in an open state, after inserting the needle into its position and prior to closing the needle head holder.

FIG. 9B shows the needle head holder 60 in its open state, after the needle has been inserted into the central channel 6522 of the strips 652, and prior to securing of the needle head 605 within the NHH 60 by closing the securing portion 620 thereon. Closing of the securing portion 620 on the needle head 605 may be carried out by pivoting the securing portion 620 about an axis of rotation until its longitudinal axis is aligned with the longitudinal axis of the receiving portion 610. The securing portion 620 is then linearly moved downwardly along the body portion 612 until the cover 6204 contacts the proximal end of the needle head 605 and the needle head 605 is effectively clamped between the base of the body portion 612 and the cover element 6204 of the securing portion 620.

Figure 9C:
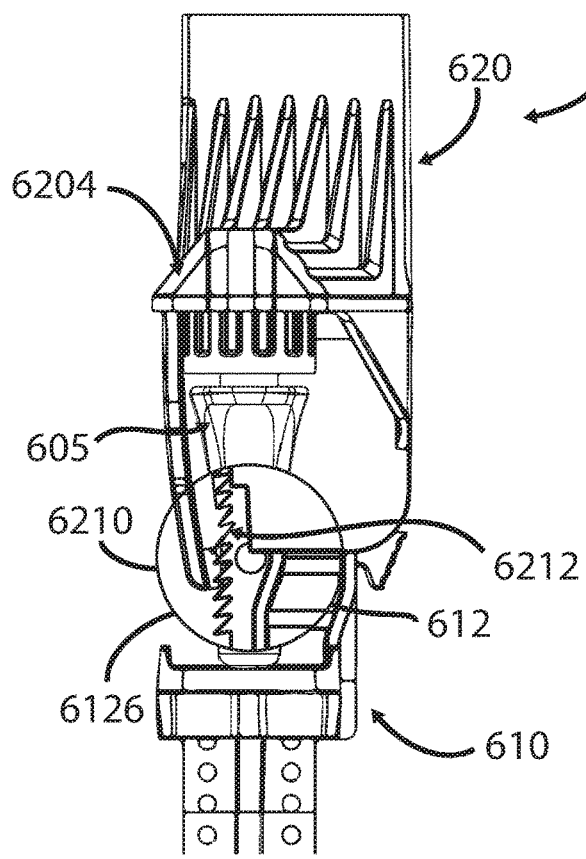
FIG. 9C shows the needle head holder of FIG. 6 in a closed state, with the needle secured therein.

FIG. 9C shows the needle head holder 60 in its closed state, after securing the needle head 605 within the NHH 60 by closing the securing portion 620 thereon. The securing portion 620 has now been moved downwardly, so that the cover element 6204 contacts the proximal end of the needle head 605, and the needle head 605 is clamped between the base of the body portion 612 and the cover element 6204. The teeth 6212 of the locking pawl 6210 then remain engaged with the ratchet teeth 6126 of the body portion 612, as shown in the encircled window, until released by the user, to prevent unintentional movement of the securing portion 620 upward and away from the needle head 605.

The contact between the cover element 6204 and the proximal end of the needle head 605 may be such that the inner shape of the cover 6204 matches the outer shape of the needle head 605, or it may be via a plurality of tangent points or lines between the inner portion of the cover 6204 and the needle head 605, to accommodate different needle head shapes and sizes. The locations of the tangent points/lines may vary according to the shape and size of the needle head in use.

Figure 9D:
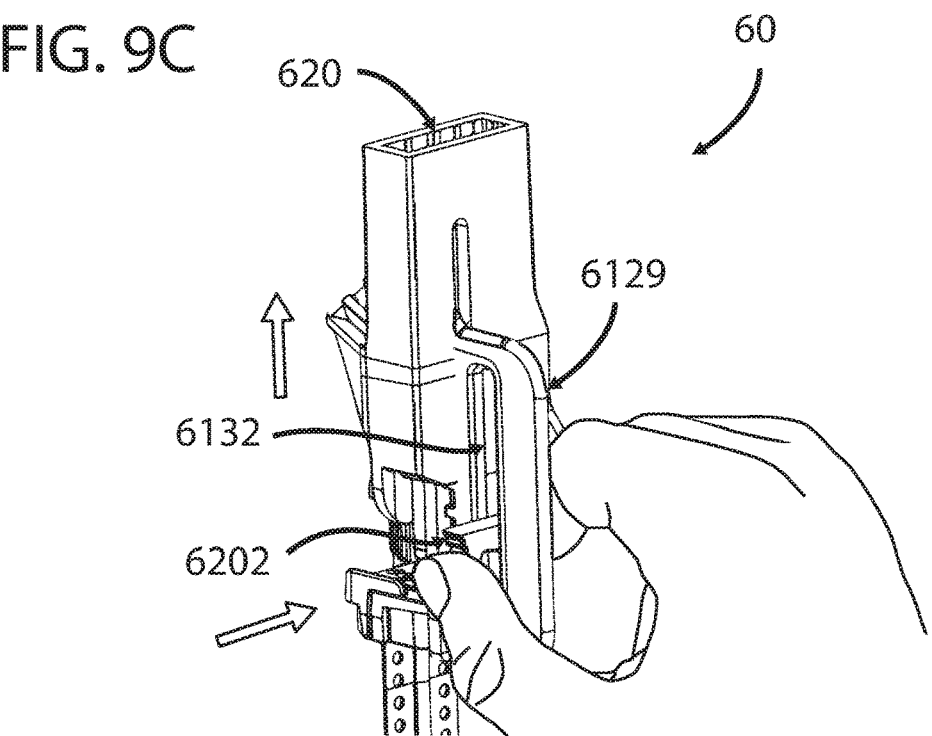
FIG. 9D shows the needle head holder of FIG. 6 being opened by the user.

FIG. 9D shows controlled disengagement of the securing portion 620 from the needle head 605 and opening of the NHH 60. In some implementations, the user presses the release lever 6202 to release the locking pawl from the ratchet teeth of the receiving portion. The user then pushes the release lever 6202 upwards, while maintaining it pressed, resulting in the displacement of the entire securing portion 620 upwards and away from the needle head 605. By continuously pushing the pressed release lever 6202 upwardly, the securing portion 620 follows its curved displacement path, as dictated by the one or more grooves formed in the body portion and the one or more protrusions of the securing portion 620, which are fitted within the groove/s, as shown hereinabove in FIG. 9A.

The securing portion 620 reaches its maximal open state when the teeth of the locking pawl are captured within the depression of the body portion, as shown hereinabove in FIGS. 9A and 9B.

Figure 9E:
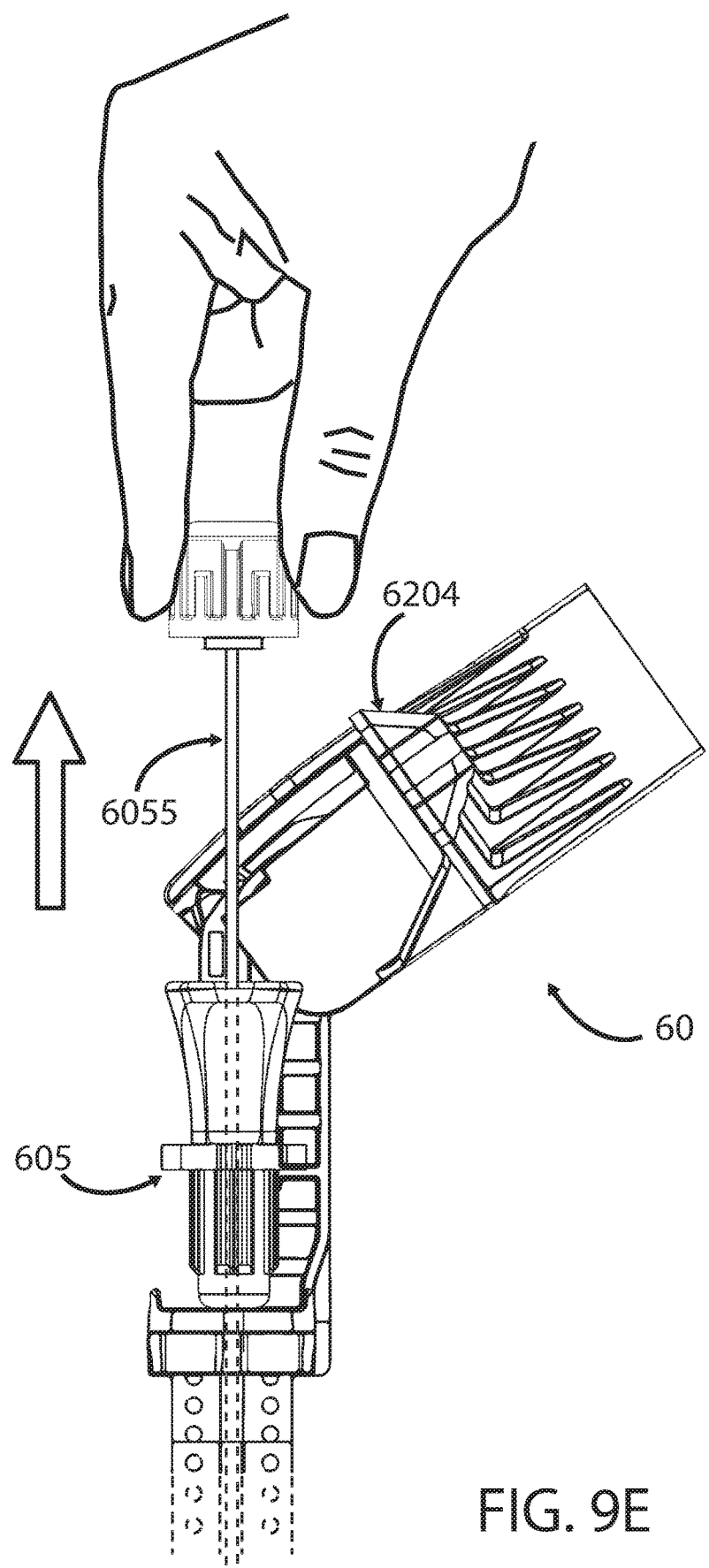
FIG. 9E shows the needle head holder of FIG. 6 in an open state and the user removing the core of the needle.

FIG. 9E shows the needle head holder 60 in its open state and the user removing the core 6055 of an introducer in order to insert a biopsy needle through the introducer, for example. In some implementations, in order to avoid the need to open the NHH 60 to remove the core 6055, or access the needle head 605 for any other purpose, the cover 6204 may include a top/upper opening, which provides access to the needle head 605 even when the NHH 60 is closed. For example, the cover 6204 may have an annular shape (not shown). Maintaining the NHH 60 closed until completion of the medical procedure minimizes the risk of undesired needle movements throughout the procedure.

Alternative implementations of the needle head holder may be adapted to receive and support different types of medical instruments.

Figure 10:
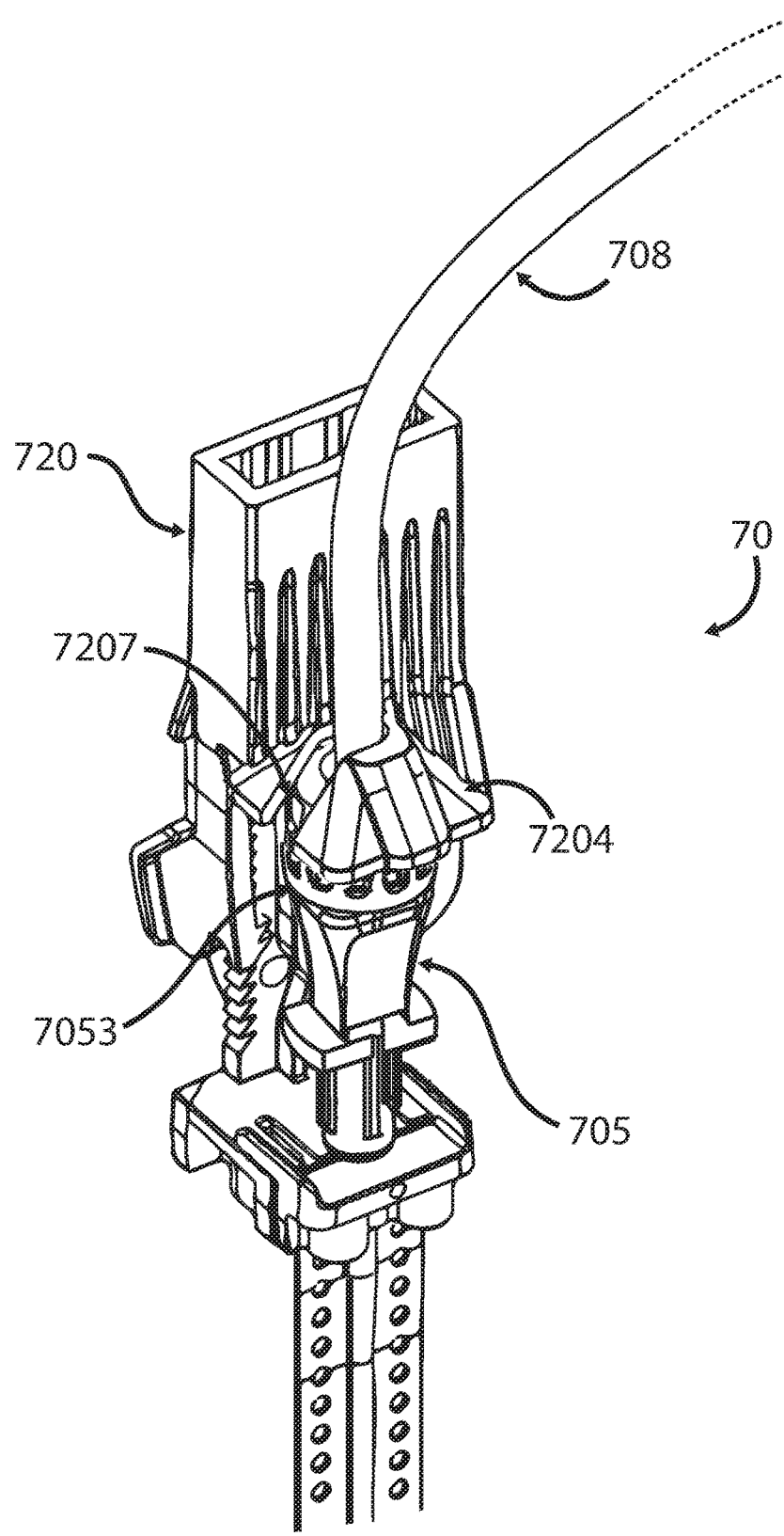
FIG. 10 shows a perspective upper view of an exemplary needle head holder with a cover portion having a slit for receiving electrical wiring of a medical instrument.

FIG. 10 shows a perspective upper view of an exemplary needle head holder 70 which includes a slit 7207 in the cover 7204 of the securing portion 720, to enable receiving a medical tool having at least one electrical wire 708 attached to it. Such tools may include, for example, introducers having optic fiber/s coupled to their cores (not shown). The optic fiber/s may be used, for example, to measure the deflection of the introducer's tip. Once in position, the core with the optic fiber/s is removed, and a biopsy needle, for example, is inserted through the introducer. In such implementations, the electrical wire 708 may be attached to the core via the upper portion 7053 of the introducer head 705.

Figure 11A:
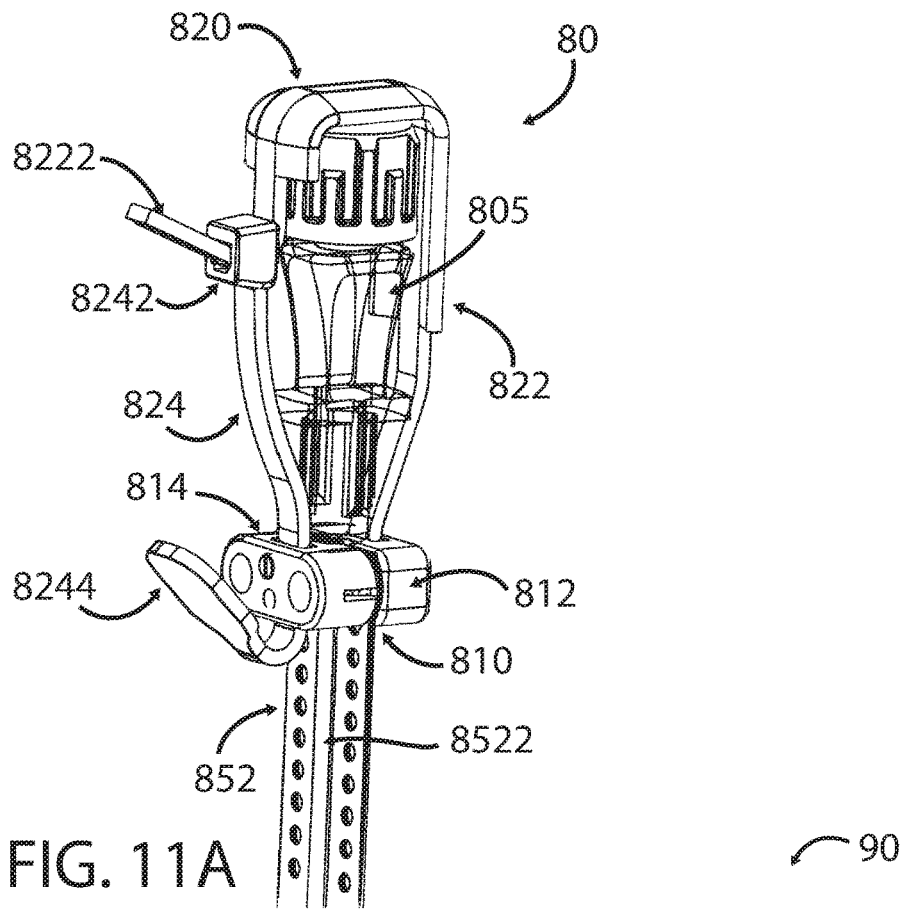
FIGS. 11A-11B show perspective views of another exemplary needle head holder having an adjustable cover portion.

FIG. 11A shows a perspective view of another needle head holder 80 having a cover portion 822. In this implementation, another form of ratchet mechanism—a zip-tie mechanism—is utilized for adjusting the NHH 80 according to the size and/or shape of the needle head in use. The NHH 80 may comprise an anchoring portion 810, which supports the distal end of the needle head 805 and anchors the proximal ends of the strips 852 thereto, and a securing portion 820, which is displaced by the user once the needle head 805 is in its proper position, in order to secure the needle head therein. The anchoring portion 810 may be one-piece or it may comprise two or more units 812 and 814 coupled together, as shown in FIG. 11A. The securing portion 820 may include a cover portion 822 and a locking portion 824. The cover portion 822 may be connected to unit 812 of the anchoring portion 810, and the locking portion 824 may be connected to unit 814 of the anchoring portion. The cover portion 822 may include a tape 8222 with teeth/ridges (not shown) that engage with a pawl (not shown) in a head member 8242 of the locking member 824. The tape 8222 can be pulled by the user in order to tighten the NHH's grip over the needle head. The locking portion 824 may further include a tab 8244, that the user can pull in order to pull apart unit 814 from unit 812, thus decoupling the two units of anchoring portion 810, as shown in FIG. 13C hereinbelow, and allowing removal of the NHH 80 from the needle head 805.

Figure 11B:
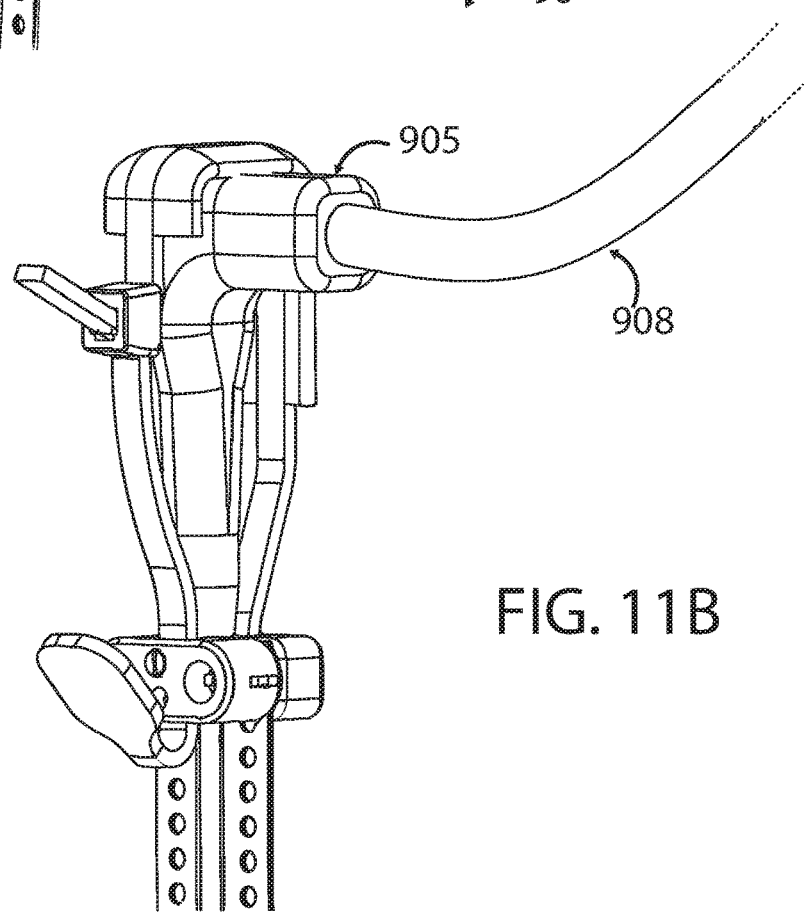

FIG. 11B shows a needle head holder 90 similar to the needle head holder 80 of FIG. 11A, but which is adapted to receive and secure an ablation catheter handle 905 with its attached wiring 908. Such an NHH 90 may be larger than an NHH 80 which is designed to receive a standard needle and/or introducer, as shown in FIG. 11A, for example, to accommodate the larger size of the handle 905. It can be appreciated that other types of medical tools may also be used with either the NHH 80, NHH 90, or any other similar implementation of the "zip-tie" NHH design.

Figure 12:
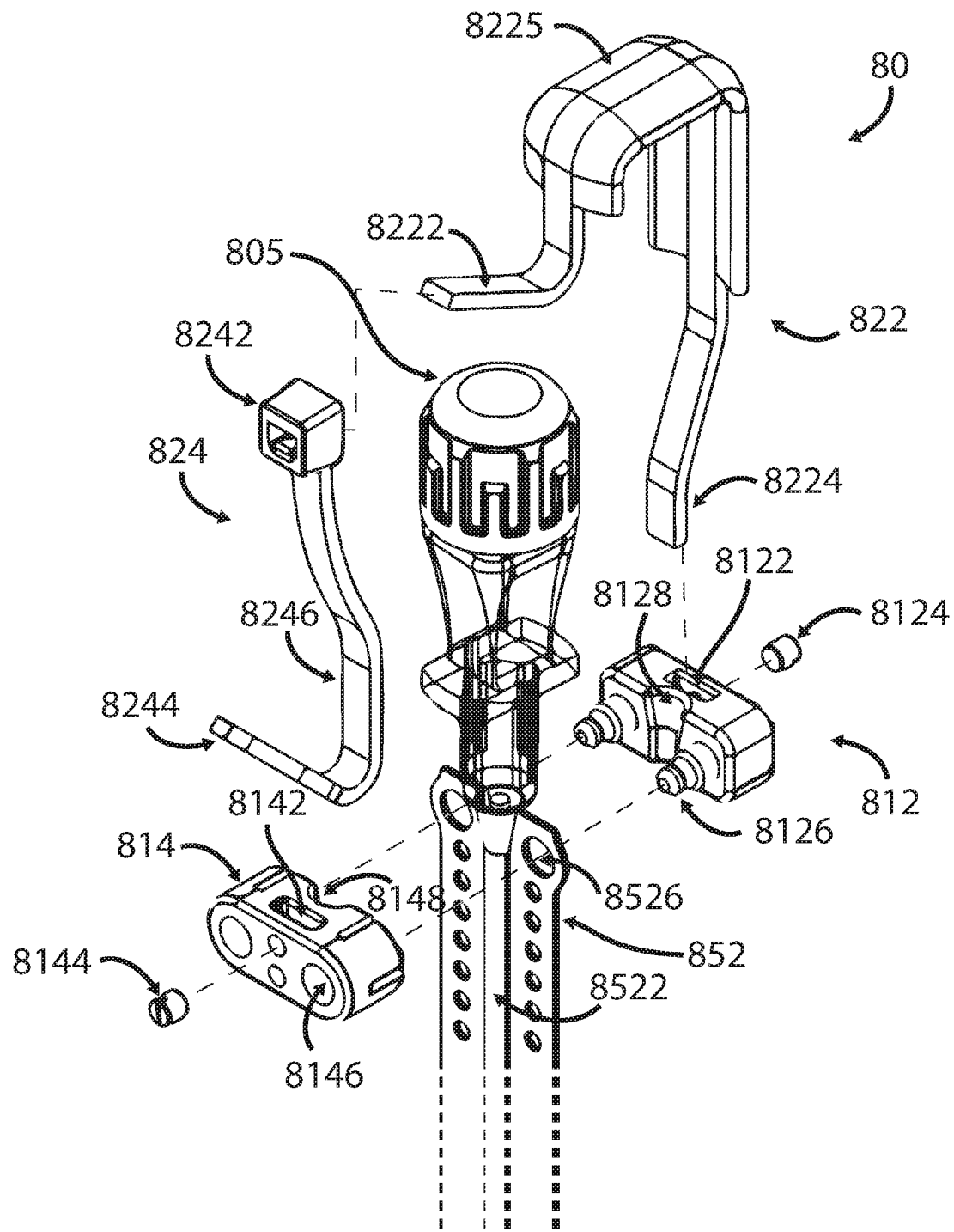
FIG. 12 shows an exploded view of the needle head holder of FIG. 11A.

FIG. 12 shows an exploded view of the needle head holder 80 of FIG. 11A, with the needle and the strips 852. Coupling between the two units 812, 814 of the anchoring portion 810 may be established, for example, using a snap-fit mechanism. One of the two units, in this case unit 812 which will be referred to hereinafter also as "the male unit", may include one or more pins 8126 which can be passed through one or more holes 8526 in at least one of the strips 852 and then mate with corresponding one or more sockets 8146 in the second unit, in this case unit 814 which will be referred to hereinafter also as "the female unit", with the strips 852 being anchored therebetween. It can be appreciated that the pins 8126 may alternatively be part of unit 814 and the sockets 8146 part of unit 812. In some implementations, units 812 and 814 may be provided to the user already coupled together, with the strips anchored therebetween, such that closing of the NHH 80 is done via coupling of the cover portion 822 and the locking portion 824. In such cases, once the needle has been inserted into the strips' central channel 8522, and the needle head 805 is properly positioned on the anchoring portion 810, the user pulls the cover portion 822 over the needle head 805, inserts the tape 8222 into the head member 8242, and pulls the free end of the tape 8222 until the needle head 805 is firmly secured within the NHH 80. In other implementations, the NHH 80 may be provided with the cover and locking portions 822, 824 coupled together, such that closing of the NHH 80 is done by coupling the two units 812 and 814 (as shown, from a decoupling perspective, in FIG. 13C hereinbelow). In such cases, the ratchet engagement between the tape 8222 and the head member 8242 is used only for tightening the NHH's grip on the needle head 805, by pulling the free end of the tape 8222 after closing the NHH 80 over the needle head 805.

In some implementations, once the tape 8222 is engaged with the head member 8242, the zip-tie mechanism cannot be undone. In other implementations, the mechanism may include a releasing element (not shown), that can be used to release the tape 8222 from the head member 8242, either for loosening the grip of the NHH over the needle head 805 or to remove at least the cover portion 822 from the needle head and allow access to the needle head 805.

The cover and locking portions 822, 824 may be flexible, at least in part, so as to adjust according to the size and/or shape of the needle head 805 in use.

In some implementations, the cover portion 822 may include a rigid end 8224 which is inserted into a corresponding slot 8122 in the male unit 812 of the anchoring portion 810. One or more screws 8124 may then be used to tightly hold the rigid end 8224 against the opposite inner wall of the slot 8122 and prevent the disconnection of the cover portion 822 from the male unit 812. Similarly, the locking portion 824 may include a rigid section 8246, located between the head member 8242 and the tab 8244, which is inserted into a corresponding slot 8142 in the female unit 814 of the anchoring portion 810, and one or more screws 8144 may be used to tightly hold the rigid section 8246 against the opposite inner wall of the slot 8142 and prevent the disconnection of the locking portion 824 from the female unit 814. In other implementations, the cover portion 822 and the male unit 812 of the anchoring portion may be manufactured as a single integral unit, and the locking portion 824 and the female unit 814 of the anchoring portion 810 may be manufactured as a single integral unit.

The male and female units 812, 814 may include a channel for enclosing the needle therein. The channel may be located in one of the two units 812, 814, or it may be formed by corresponding grooves 8128, 8148 in the male and female units 812, 814, respectively, upon coupling of the two units. The channel may be sized to receive needles with a specific gauge or, in case the NHH 80 is configured to receive a variety of needles having needle heads of different shapes and sizes, it may be sized according to the largest needle gauge which can be used with the NHH 80.

In some implementations, the proximal portion of the channel may have a conical shape in order to ease the insertion of the needle into the central channel 8522 of the strips 852. The proximal portion of the strips' central channel 8522 may also have a conical shape.

Figures 13A, 13B:
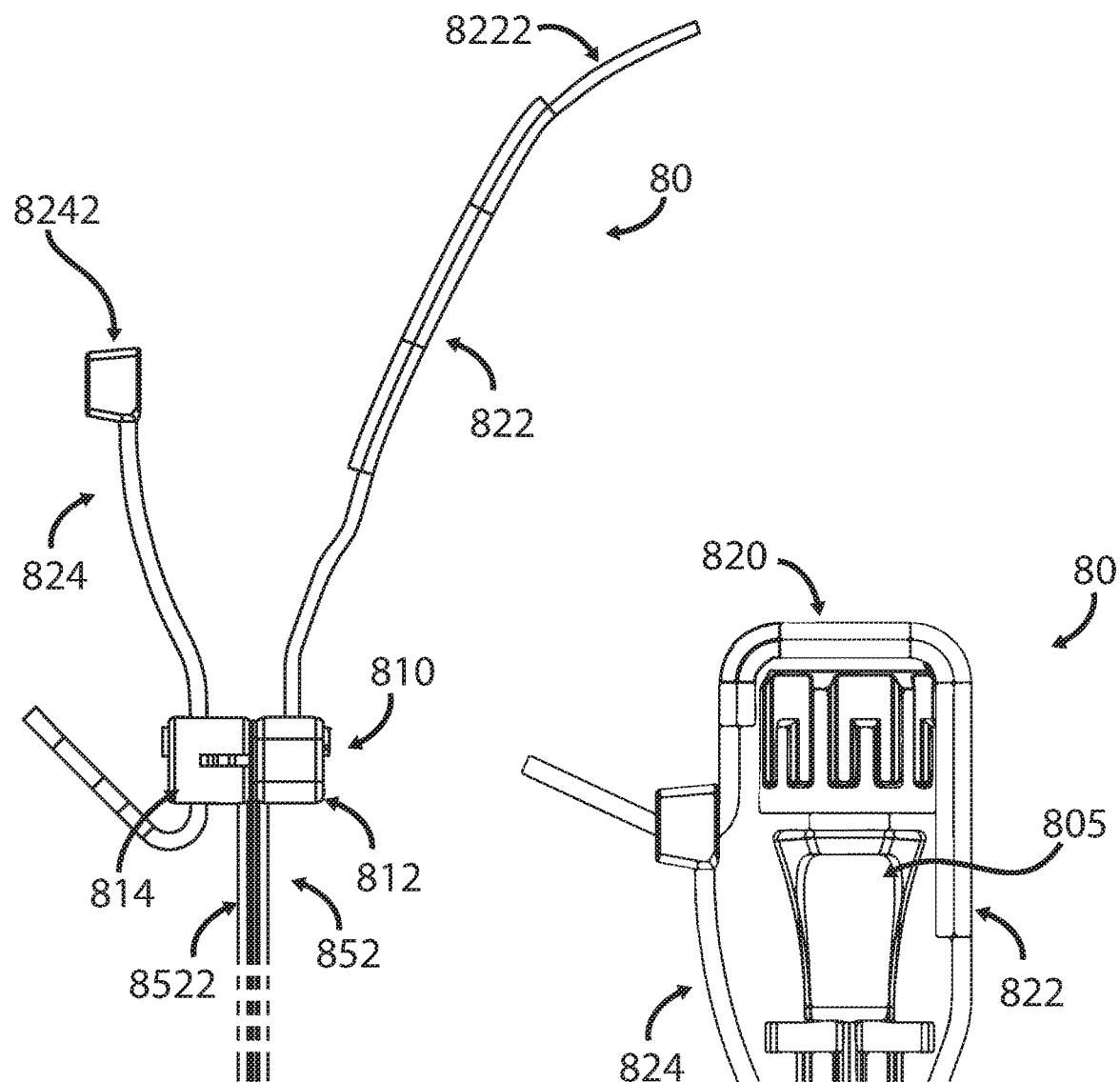
FIG. 13A shows the needle head holder of FIG. 11A in an open state, prior to coupling the needle to the needle head holder.
FIG. 13B shows the needle head holder of FIG. 11A in a closed state, with the needle secured therein.
Figure 13C:
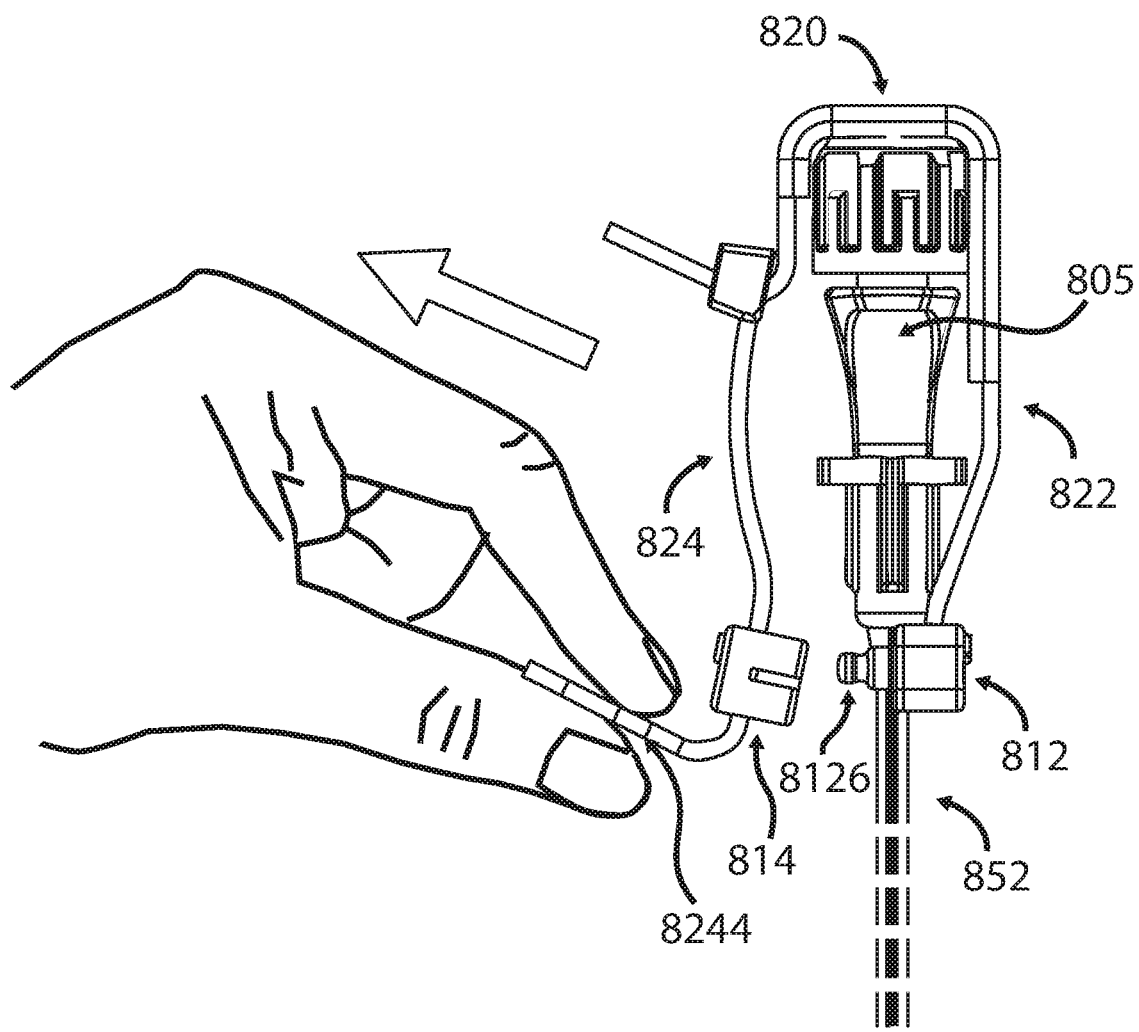
FIG. 13C shows the needle head holder of FIG. 11A being decoupled from the needle head.

FIG. 13A shows the needle head holder 80 in its open state, prior to insertion of the needle into the central channel 8522 of the strips 852 and securing of the needle head to the NHH 80. Once the user inserts the needle all the way into the strips' central channel 8522, such that the needle head rests on the anchoring portion 810 of the NHH 80, the user couples together the cover and locking portions 822, 824 by pulling the cover portion 822 over the needle head and then inserting the tape 8222 of the cover portion 822 into the head member 8242 of the locking portion 824 and tightening their grip of the needle head by pulling the free end of the tape 8222 emerging from the other side of the head member 8242.

In other implementations, the NHH 80 may be provided with the cover and locking portions 822, 824 coupled together, such that closing of the NHH 80 is done by coupling the male and female units 812 and 814.

FIG. 13B shows the needle head holder 80 in its closed state, after insertion of the needle into the central channel 8522 of the strips 852 and securing the needle head 805 to the NHH 80 by closing the securing portion 820 thereon.

FIG. 13C shows decoupling of the needle head holder 80 from the needle head 805. In some implementations, the user pulls the tab 8244 of the locking portion 824 to disconnect the female unit 814 from the male unit 812. The pin/s of the male unit 812 can then be removed from the hole/s at the proximal end of the strips 852, and the entire NHH 80 can be removed from the needle head 805. In other implementations, the zip-tie mechanism may include a releasing element (not shown) for releasing the tape from the head member and allowing removal of the cover portion 822 from the needle head 805.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A device for securing a medical tool selected from medical tools having different head member configurations and configured for insertion into a tissue of a subject, the device comprising:
   two or more housing portions configured to receive a head member of any of said medical tools; and
   an adjustment mechanism configured to adjust at least one of the height and the shape of at least a portion of the device according to at least one of the height and the shape of said head member;
   wherein:
   at least one of said two or more housing portions is configured to be moved relative to at least another of said two or more housing portions, to transition the device at least one of from an open state to a closed state and from a closed state to an open state,
   at least one of said two or more housing portions comprises a cover element configured to establish contact with a proximal end of said head member upon activation of said adjustment mechanism, and
   when said two or more housing portions have received said head member and are in the closed state, and the adjustment mechanism has been activated, there is essentially no relative movement between said two or more housing portions and said head member.

2. The device of claim 1, further comprising a locking mechanism configured to lock together at least two of said two or more housing portions when the device is in its closed state.

3. The device of claim 2, wherein said locking mechanism comprises at least one of: a latch, a locking pin, a ratchet mechanism and a snap-fit mechanism.

4. The device of claim 1, wherein said adjustment mechanism comprises a ratchet mechanism.

5. The device of claim 4, wherein said ratchet mechanism comprises ratchet teeth disposed on at least one of said two or more housing portions and a locking pawl on at least another of said two or more housing portions, said locking pawl being configured to engage with said ratchet teeth.

6. The device of claim 5, further comprising a release member configured to disengage said locking pawl from said ratchet teeth.

7. The device of claim 1, wherein at least two of said two or more housing portions are coupled together via a hinge.

8. The device of claim 1, wherein the movement of said at least one of said two or more housing portions relative to said at least another of said two or more housing portions comprises at least one of linear movement and rotational movement.

9. The device of claim 1, further comprising one or more anchoring elements configured to attach a collapsible support guide of said medical tool to at least one of said two or more housing portions, said one or more anchoring elements comprising one or more protrusions.

10. The device of claim 9, wherein said collapsible support guide comprises a pair of flexible strips connected along at least a portion of their length and having a central channel therebetween configured to receive and support said medical tool.

11. A device for securing a medical tool selected from medical tools having different head member configurations and configured for insertion into a tissue of a subject, the device comprising:
    a first housing portion configured to receive at least a portion of a head member of any of said medical tools;
    a second housing portion coupleable to said first housing portion, said second housing portion being configured to be moved relative to said first housing portion at least one of from an open state of the device to a closed state of the device and from a closed state of the device to an open state of the device; and
    an adjustment mechanism configured to adjust at least one of the height and shape of at least a portion of the device, according to at least one of the height and shape of said head member,
    wherein at least one of said first and second housing portions comprises a cover element configured to establish contact with a proximal end of said head member upon activation of said adjustment mechanism.

12. The device of claim 11, wherein said adjustment mechanism comprises a ratchet mechanism.

13. The device of claim 11, wherein the movement of said second housing portion relative to said first housing portion comprises at least one of linear movement and rotational movement.

14. The device of claim 13, wherein said second housing portion comprises a protrusion, and a wall of said first housing portion comprises a niche configured to receive said protrusion, and wherein said rotational movement comprises pivoting of said second housing portion relative to said first housing portion, upon said protrusion being received within said niche.

15. The device of claim 11, further comprising one or more anchoring elements configured to attach a collapsible support guide of said medical tool to at least one of said first and second housing portions, wherein said one or more anchoring elements comprise one or more protrusions, and said collapsible support guide comprises a pair of flexible strips connected along at least a portion of their length and having a central channel therebetween configured to receive and support said medical tool.

16. The device of claim 15, wherein said cover element is configured to maintain said head member concentric with said central channel.

17. A method for securing a first medical tool selected from medical tools having different head member configurations and configured for insertion into a tissue of a subject, the method comprising:
    inserting said first medical tool, having a first head member, into an opening in at least one of two or more housing portions of a holder device, until a distal end of said first head member is supported by said at least one of said two or more housing portions;
    displacing at least one of said two or more housing portions to transition said holder device from an open state to a closed state; and
    adjusting at least one of the height and shape of at least a portion of said holder device according to at least one of the height and shape of said first head member, such that there is essentially no relative movement between said two or more housing portions and said first head member,
    wherein upon execution of said adjusting, a cover element of at least one of said two or more housing portions establishes contact with a proximal end of said head member.

18. The method of claim 17, further comprising the steps of:
    displacing at least one of said two or more housing portions to transition said holder device from the closed state to the open state;
    removing said first medical tool from said holder device;
    inserting a second medical tool, having a second head member having a configuration different from the configuration of said first head member of said first medical tool, into said opening, until a distal end of said second head member is supported by said at least one of said two or more housing portions;
    displacing at least one of said two or more housing portions to transition said holder device from an open state to a closed state; and
    adjusting at least one of the height and shape of at least a portion of said holder device according to at least one of the height and shape of said second head member, such that there is essentially no relative movement between said two or more housing portions and said second head member.

19. The method of claim 17, wherein said adjusting is executed using a ratchet mechanism.

* * * * *